United States Patent
Yuan et al.

(10) Patent No.: US 7,273,617 B2
(45) Date of Patent: Sep. 25, 2007

(54) INFECTIOUS CDNA CLONES OF PORCINE REPRODUCTIVE AND RESPIRATORY SYNDROME VIRUS AND EXPRESSION VECTORS THEREOF

(75) Inventors: Shishan Yuan, St. Paul, MN (US); Shi-jun Ma, Shoreview, MN (US)

(73) Assignee: ProtaTek International, Inc., St. Paul, MN (US)

( * ) Notice: Subject to any disclaimer, the term of this patent is extended or adjusted under 35 U.S.C. 154(b) by 398 days.

(21) Appl. No.: 10/977,375

(22) Filed: Oct. 29, 2004

(65) Prior Publication Data

US 2005/0238661 A1    Oct. 27, 2005

Related U.S. Application Data

(63) Continuation of application No. 10/346,004, filed on Jan. 16, 2003, now Pat. No. 6,841,364.

(60) Provisional application No. 60/351,310, filed on Jan. 22, 2002.

(51) Int. Cl.
*A61K 39/12* (2006.01)
(52) U.S. Cl. .................. 424/204.1; 435/91.1; 435/320.1
(58) Field of Classification Search .............. 424/204.1, 424/205.1, 194.1; 435/91.1, 320.1
See application file for complete search history.

(56) References Cited

U.S. PATENT DOCUMENTS

| | | |
|---|---|---|
| 5,476,778 A | 12/1995 | Chladek et al. |
| 5,510,258 A | 4/1996 | Sanderson et al. |
| 5,587,164 A | 12/1996 | Sanderson et al. |
| 5,677,429 A | 10/1997 | Benfield |
| 5,683,865 A | 11/1997 | Collins et al. |
| 5,840,563 A | 11/1998 | Chladek et al. |
| 5,846,805 A | 12/1998 | Collins et al. |
| 5,989,563 A | 11/1999 | Chladek et al. |
| 5,998,601 A | 12/1999 | Murtaugh et al. |
| 6,015,663 A | 1/2000 | Wesley et al. |
| 6,033,844 A | 3/2000 | Visser et al. |
| 6,042,830 A | 3/2000 | Chladek et al. |
| 6,080,570 A | 6/2000 | Chladek et al. |
| 6,110,468 A | 8/2000 | Collins et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,498,008 B2 | 12/2002 | Collins et al. |
| 6,500,662 B1 | 12/2002 | Calvert et al. |
| 6,855,315 B2 | 2/2005 | Collins et al. |
| 7,132,106 B2 * | 11/2006 | Calvert et al. ........... 424/205.1 |
| 2004/0208899 A1 | 10/2004 | Collins et al. |

FOREIGN PATENT DOCUMENTS

| | | |
|---|---|---|
| EP | 000839912 A1 | 5/1998 |
| EP | 1 018 557 A2 | 7/2000 |
| WO | WO 01/55353 A2 | 8/2001 |

OTHER PUBLICATIONS

Boyer, Jean-Christophe et al., "Infectious transcripts and cDNA clones of RNA viruses," Virology 198: 415-426 (1994).
Collins et al., "Isolation of swine infertility and respiratory syndrome virus (Isolate ATCC-VR2332) in North America and experimental reproduction of the disease in gnotobiotic pigs," J. Vet Diagn Invest 4:117-126(1992).
Conzelmann, Karl-Klaus et al., "Genetic engineering of animal RNA viruses," Elsevier Science Ltd, 386-393 (1996).
Palese, Peter, "Genetic engineering of infectious negative-strand RNA viruses," Elsevier Science Ltd., 3:4, 123-125 (Apr. 1995).
Snijder, EJ and Meulenberg, JJ, The molecular biology of arteriviruses, J.Gen Virol 79:961-979 (1988).
Wensvoot, et al., "Mystery swine disease in the Netherlands: the isolation of Lelystad virus," Vet Q 13: 121 (1991).
GenBank Accession # AF184212, 2000.
GenBank Accession # U87932, 1998.
Yuan et al., "Heteroclite subgenomic RNAs are produced in procine reproductive and respiratory syndrome virus infection" Virology 275, 158-169 (2000).
Allende, R. et al., "Mutations in the genome 7 of porcine reproductive and respiratory syndrome virus responsible for the attenuation phenotype," Archives of Virology (2000) 145(6):1149-1161.
Meulenberg et al.; "Infectious transcripts from cloned genome-length cDNA of porcine reproductive and respiratory syndrome virus," J. Virol. (1998) 71(1):380-387.
Nielsen, H.S. et al., "Generation of an infectious clone of VR-2332, a highly virulent North American-type isolate of porcine reproductive and respiratory syndrome virus," J. Virol. (2003) 77(6):3702-3711.
Shen, S. et al., "Determination of the complete nucleotide sequence of a vaccine strain of porcine reproductive and respiratory syndrome virus and identification of the Nsp2 gene with a unique insertion," Archives of Virology (2000) 145(5):871-883.

* cited by examiner

*Primary Examiner*—Ali R. Salimi
(74) *Attorney, Agent, or Firm*—Michael Best & Friedrich LLP

(57) ABSTRACT

Infectious cDNA clones of North American Porcine Reproductive and Respiratory Syndrome Virus (PRRSV) are provided. Further provided are cDNA clones comprising genetic mutations. Also provided are vaccines comprising cDNAs, including genetically and immunologically marked vaccines for North American PRRSV.

9 Claims, 11 Drawing Sheets

FIG 1. Summary Of Genetic Modifications Of Infectious cDNA.

| Name mutated clone | Nature of mutations | Mutation site | Genetic marker (Enzyme sites) |
|---|---|---|---|
| pM5CE | substitution ORF 5, 2 aa changes | 14305, T to G 14307, A to G | Mlu I |
| pNU | insertion | 15382 ATG | Nde I |
| pUPS | insertion deletion | 15382 15369-15375 | Pac I, Asc I |
| pCTSA2 | insertion | Junction of ORF1 &2 12181 | Pac I, Swa I, Asc I, Vsp I |
| pCPV2 | insertion of PCV II ORF 2 | 12181 | |
| pSD2 | Deletion | 5' part of ORF2 12358-12583 | Swa I, Pac I, Asc I |
| pSD4 | Deletion | Middle of ORF4 13619-13793 | Swa I, Pac I, Asc I |

FIG. 2. PRRSV genomic organization and cloning strategy

FIG. 3. Restriction enzyme digestion of RT-PCR products revealed the the transfectant viruses contain expected mutations
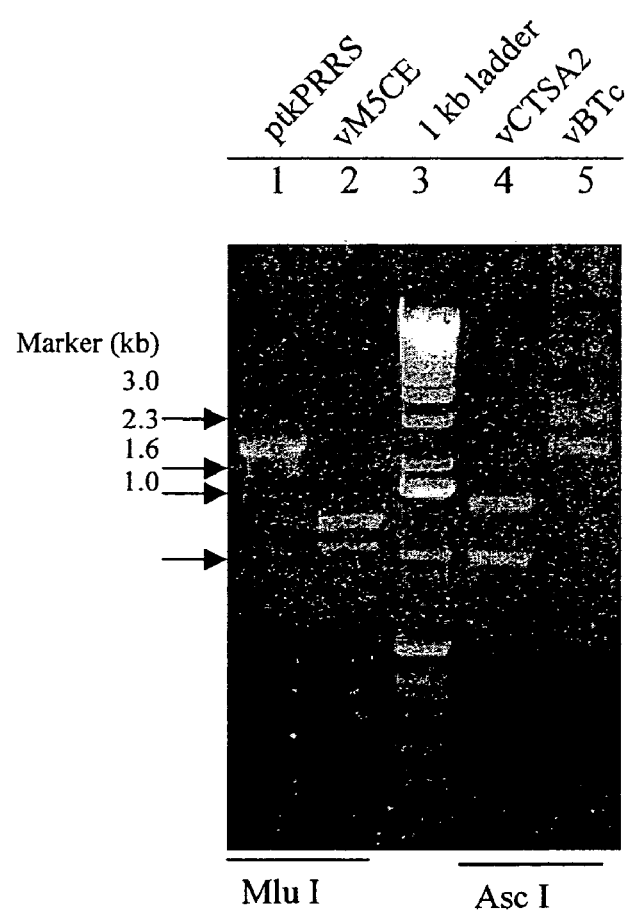

```
        14280       14290       14300       14310       14320       14330
        +----------+----------+----------+----------+----------+
        GAAGAACTGTATGTCCTGGCGCTACTCATGCACCAGATACACCAACTTTCT   ptkPRSV
        ..........................G.G.....................   vM5CE RT-PCR
                                  Mlu I
```

B) vNUa

```
          15360       15370       15380       15390       15400
          +----------+----------+  ----------+----------+------
          CTCAGCATGATGGGCTGGCAT---TCTTGAGGCATCTCAGTGTTTGAATT   ptkPRRS
          ....................ATG.................. ........  vNUa RT-PCR
                              Nde I
```

C) vUPS4

```
         15350       15360       15370           15380       15390
         +----------+----------+--        -------+----------+----
         CACAGCATCACCCTCAGCATGAT--------GGGC-TGGCATTCTTGAGGC   ptkPRRS
         ............A-........TTAATTAA....GC.C.............   pUPS4
         ............A-........TTAATTAA....GC.C.............   vUPS RT-PCR
                               Pac I        Asc I
```

D) vCTSA

```
         12170     12180                              12190
         -+--------+                             ---------+----
         GGCCTGAATTGA----------------------AATGAAATGGGGTCC   ptkPRRS
         ............TTAATTAATTTAAATGGCGCGCC..............   vCTSA RT-PCR
                      Pac I   Swa I   Asc I
```

FIG. 5A. vCPV2 expressing partial ORF2 of PCV II.
RE mapping of RT-PCR products of vCPV2

→ 3.0 kb
→ 2.3 kb
→ 1.6 kb
→ 1.0 kb

Primer pair: SF11210 / SR 13334
Samples:
vCPV2 (lane 1, 2)
vCTSA2 (lane 4, 5)

FIG. 5B

```
                      PRRSV            PRRSV
                      ORF1b            ORF1b
                      stop             Start 12182
                      ←⎯⎯⎯             ⎯⎯⎯→
  1   TAGGCCTGAATTGATTAATTAAATGACGTATCCAGGGAGGCGTTACCGCAGAAGAAGACA   pCPV2
  1   ............................................................   vCPV2
                  Pac I
 39   CCGCCCCCGCAGCCATCTTGGCCAGATCCTCCGCCGCCGCCCCTGGCTCGTCCACCCCCG   pCPV2
 39   ............................................................   vCPV
 99   CCACCGCTACCGTTGGAGAAGGAAAAATGGCATCTTCAACACCCGCCTCTCCCGCACCTT   pCPV2
 99   ...........----------------------------------------------------   vCPV2
159   CGGATATACTGTCAAGCGTACCACAGTCACAACGCCCTCCTGGGCGGTGGACATGATGAG   pCPV2
115   ------------------------------------------------------------   vCPV2
219   ATTTAAGCTTGACGACTTTGTTCCCCGGGAGGGGGGACCAACAAAATCTCTATACCCTT    pCPV2
115   ------------------------------------------------------------   vCPV2
279   TGAATACTACAGAATAAGAAAAGTTAAGGTTGAATTCTGGCCCTGCTCCCCCATCACCCA   pCPV2
115   ------------------------------------------------------------   vCPV2
339   GGGTGATAGGGGAGTGGGCTCCACTGCTGTTATTCTAGATGATAACTTTGTACCAAAGGC   pCPV2
115   ------------------------------------------------------------   vCPV2
399   CAATGCCCTAACCTATGACCCATATGTAAACTACTCCTCCCGCCATACAATCCCCCAACC   pCPV2
115   ------------------------------------------------------------   vCPV2
459   CTTCTCCTACCACTCCCGTTACTTCACACCCAAACCTGTTCTTGACTCCACTATTGATTA   pCPV2
115   --------------------------------------------------............   vCPV2
519   CTTCCAACCAAATAACAAAAGGAATCAGCTTTGGATGAGGATACAAACCTCTAGAAATGT   pCPV2
128   ............................................................   vCPV2
579   GGACCACGTAGGCCTCGGCACTGCGTTCGAAAACAGTAAATACGACCAGGACTACAATAT   pCPV2
188   ............................................................   vCPV2
639   CCGTGTAACCATGTATGTACAATTCAGAGAATTTAATCTTAAAGACCCCCCACTTAAACC   pCPV2
248   ............................................................   vCPV2
               Asc I
699   CTAAGGCGCGCCAATGAAATGGGGTCCATGC                                pCPV2
312   ..⌊C⌋........⌊...⌋..............                               vCPV2
      PCV ORF       PRRSV ORF2
      Stop codon    Start codon
```

FIG. 5C. The stop codon of the inserted PCV capsid gene was mutated in recombinant PRRSV pCPV2 plasmid T T A A  A C C C T A A G G C G C G C C A | A T G  A A  A T G G
         750            760              770 vCPV2 RT-PCR

C T T A A  A C C C T C A G G C G C G C C A | A T G  A A A  T G G
          360            370              380
              PCV ORF 2 stop    AscI    PRRSV ORF 2

FIG. 6. Northern blot showed genetic markers inserted into PRRSV

A. PSA probe

B. PCV probe

Genomic RNA mRNA2

```
    12170         12180                              12190
 -+---------+                        ----------+----
GGCCTGAATTGA-----------------------AATGAAATGGGGTCC   ptkPRRS
............TTAATTAATTTAAATGGCGCGCC...............   vCTSA RT-PCR
............TTAATTAATTTAAATGGCGCGCC...............   serum RT-PCR
            Pac I         Swa I   Asc I
```

FIG. 8. Immunofluroscence Assay (FA) showed that transfectant PRRS viruses were generated.

A). vptkPRRS

B). vCTSA

C). vCPV2

D). mock

FIG.9. Indirect Immunofluroscence (IFA) showed expression of PCV capsid gene in recombinant PRRSV.

A). vCPV2

B). vptkPRRS

C). mock

INFECTIOUS CDNA CLONES OF PORCINE REPRODUCTIVE AND RESPIRATORY SYNDROME VIRUS AND EXPRESSION VECTORS THEREOF

CROSS REFERENCE TO RELATED APPLICATIONS

This application is a continuation of U.S. patent application Ser. No. 10/346,004, filed Jan. 16, 2003, now U.S. Pat. No. 6,841,364, incorporated herein by reference in its entirety, which claims the benefit of U.S. Provisional Patent Application Ser. No. 60/351,310, filed Jan. 22, 2002, also incorporated herein by reference in its entirety.

TECHNICAL FIELD

The present invention relates to the field of molecular virology and more particularly to the construction of recombinant nucleic acids encoding Porcine Reproductive and Respiratory Syndrome Virus (PRRSV).

BACKGROUND OF THE INVENTION

Porcine reproductive and respiratory syndrome (PRRS), originally known as "mystery swine disease," was first recognized in the 1980's in the United States. The Lelystad virus (LV) strain of PRRSV was first isolated in Europe, (Wensvoot et al., "Mystery swine disease in the Netherlands: the isolation of Lelystad virus," Vet Q 13, 121-130 (1991)) followed rapidly by the isolation of the North American prototype, strain VR-2332, in the United States (Collins et al. "Isolation of swine infertility and respiratory syndrome virus (Isolate ATCC-VR2332) in North America and experimental reproduction of the disease in gnotobiotic pigs," J. Vet Diagn Invest 4, 117-126 (1992)). The principal clinical manifestation of the disease is characterized by a sudden onset of abortion and infertility in infected sows, and increased mortality rates in piglets which may result from secondary respiratory infections.

The etiological agent capable of reproducing the disease syndrome has been classified as a member of the Arteriviridae family of viruses and has been identified as an enveloped small spherical RNA virus. The virion particle has an average diameter of about 62 nm and a 25-30 nm nucleocapsid core surrounded by an envelope. The genome of PRRSV is a single-stranded, nonsegmented, 5'-capped and 3'-polyadenylated, positive-sense RNA of 15.1-15.5 kilobases in length, encoding at least seven demonstrated open reading frames (ORFs). The coding sequences are flanked by untranslated regions (UTR) at both the 5' and 3' ends of the genome. Viral structural proteins are expressed from six subgenomic mRNAs formed by a unique, yet unknown, discontinuous transcription mechanism by which the 5' leader sequence noncontiguously joins with the body sequence located at the 3' end of the viral genome. The viral replicase is encoded by ORFs 1a/1b, with the latter expressed via a −1 frameshift from the genomic RNA. ORFs 2 to 4 encode putative structural glycoproteins. ORF 5 encodes the major envelope glycoprotein of approximately 25 kDa. A non-glycosylated membrane protein of 18 kDa is encoded by ORF 6 and the 15 kDa nucleocapsid protein is encoded by ORF 7 (Snijder, E. J. and J. J., Meulenberg, "The molecular biology of arteriviruses," J. Gen Virol 79, 961-979 (1998)).

The European and North American PRRSV genotypes are dramatically different both genetically and immunologically. Only about 45 percent nucleic acid identity and little serological cross-reaction between the genotypes have been reported. In general, European genotype PRRSV strains previously have been limited to Europe, while the viruses isolated from the rest of the world belong to the North American genotype, with ATCC VR-2332 as the prototype.

Recently, the swine industry has suffered from a severe form of PRRSV disease, characterized by increased abortion and mortality rates in pregnant sows. These atypical PRRSV outbreaks surprisingly have been reported in herds vaccinated with a commercially available live vaccine. These outbreaks clearly demonstrate a need for an improved vaccine to reduce or eliminate economic losses associated with swine morbidity and mortality caused by PRRSV disease. In addition, neurotropic PRRSV has been isolated from herds in which increased rates of abortion occurred, suggesting that PRRSV may be expanding its tissue tropism. The isolation of LV-like PRRSV in North America and the increased use of a vaccine derived from a North American strain in Europe are indications that the two genotypes of PRRSV are no longer geographically separated and are becoming endemic worldwide.

Full-length cDNA clones of positive-strand RNA viruses are important tools for the study of the biology of viruses (Boyer, J. C., "Infectious transcripts and cDNA clones of RNA viruses," Virology 198, 415-426 (1994)). Infectious cDNA can be used to tackle fundamental questions regarding the mechanism of viral replication and pathogenesis. Moreover, full-length cDNA clones can be used to produce a genetically engineered molecular vaccine with desired genetic and immunologic traits. Although an infectious cDNA has been developed for the LV strain of PRRSV, there remains a need for a full-length North American PRRSV cDNA. Because of the expanding tropism and the emergence of the North American strain in herds worldwide, an infectious clone is needed to generate a more efficient molecular vaccine against PRRSV disease.

SUMMARY OF THE INVENTION

The present invention encompasses compositions and methods that provide for the establishment of infectious, full-length cDNA clones of a North American strain of PRRSV.

As a first aspect, the present invention encompasses isolated polynucleotides comprising an infectious cDNA encoding a North American PRRSV viral RNA transcript. The invention also encompasses vectors comprising polynucleotides of the invention.

Isolated infectious cDNAs of the invention may suitably comprise mutations, including insertions, deletions and substitutions of nucleotides or polynucleotides. Isolated polynucleotides may further comprise one or more foreign polynucleotides.

As a second aspect, the present invention provides methods producing a full-length infectious North American PRRSV cDNA. The method comprises a first step of reverse transcribing viral RNAs to obtain cDNA fragments. Further steps include cloning the cDNA fragments to form primary clones, combining the primary clones to form intermediate clones and combining the intermediate clones to obtain a full-length infectious cDNA clone.

Additional methods of the invention may include introducing a genetic modification comprising effecting a nucleotide or polynucleotide substitution, insertion or deletion, or a combination thereof, in at least one of the primary or intermediate clones.

Also provided is a method of producing infectious virus particles from an isolated full-length North American PRRSV cDNA comprising the steps of producing a full-length North American PRRSV cDNA clone, inserting a eukaryotic promoter sequence upstream of the 5' end of the PRRSV cDNA to form a replication-competent clone, transforming host cells with the replication-competent clone and isolating virus particles from the host cells. The viral particles produced according to the method are also encompassed by the invention.

The present invention also encompasses compositions comprising isolated cDNAs of North American PRRSV. Suitably, cDNAs used in compositions of the invention are genetically and/or immunologically marked.

BRIEF DESCRIPTION OF THE DRAWINGS

FIG. 1 is a summary of suitable genetic modifications in accordance with the present invention.

FIG. 2 is a schematic representation of PRRSV genomic organization and cloning strategy.

FIG. 3 depicts restriction endonuclease fragment patterns of the RT-PCR products of transfectant viruses.

FIG. 4 depicts nucleotide sequence comparisons showing the expected mutations at the corresponding sites of the mutagenized plasmids from the parental clone ptkPRRS (SEQ ID NO: 1). Nucleotide sequence lineups show that transfectant viruses contain the expected mutations. "." Represents nucleotides in the query sequence match that of the subject sequence of ptkPRRS. "-" represents deletion of nucleotides. Mismatched sequences are indicated by showing the actual sequence. New restriction endonuclease recognition sequences are underlined.

FIG. 5A depicts restriction enzyme mapping of the RT-PCR products of vCPV2. FIG. 5B depicts Nucleotide sequencing showing that inserted PCV capsid gene was internally deleted. Sequences were generated from the plasmid pCPV2 and its transfectant virus RT-PCR product in the region of insertion. The insertion sites, Pac I and Asc I, and flanking PRRSV sequences are indicated. Numbers on the left indicate the coding sequences for the capsid gene of PCV type virus. "." Represents nucleotides that match that of pCPV, while "-" represents deletions. FIG. 5C presents sequence analysis results demonstrating that the stop codon of the inserted PCV capsid gene was mutated in recombinant PRRSV.

FIG. 6 depicts inserted nucleotide sequences in the corresponding genomic and subgenomic RNAs.

FIG. 8 depicts results of Immmunofluroscence assays conducted to investigate the infectivity of infectious cDNA clone ptkPRRS (SEQ ID NO: 1), as well as ptkPRRS derivatives pCTSA and pCPV2.

FIG. 9 depicts the expression of inserted PCV II capsid gene.

DETAILED DESCRIPTION OF THE INVENTION

Figures 7A, 7B:
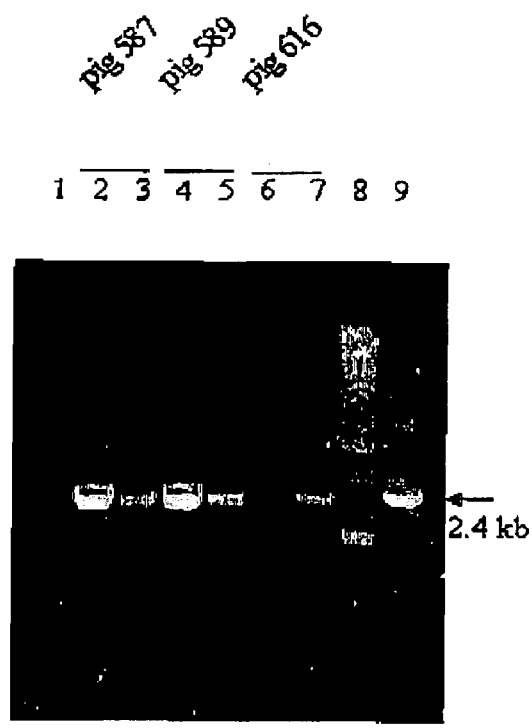
FIG. 7A depicts RT-PCR results demonstrating that vCTSA2 replicated in pigs. RT-PCR was conducted with primer pair SF11210/SR13334 from viral RNA in serum samples. Sera were collected at 7th and 14th day (lane 3, 5, 7) post infection Cell culture vCTSA was used as positive control (lane 9), while mock-infected pig serum was used as a negative control (lane 1).
FIG. 7B depicts sequence lineups showing that recombinant virus vCTSA replicated and retained genetic markers in pigs.

The present invention provides full-length cDNA clones of the North American strain of Porcine Reproductive and Respiratory Syndrome Virus. Full-length cDNA clones of positive-stranded RNA viruses have been constructed for several viral systems, but have not heretofore been reported for North American PRRSV. As will be appreciated by those of skill in the art, the infectious cDNA clones described herein provide a means by which to further elucidate the biology of this complex virus. In addition, clones of the invention can be used in the production of vaccines, for example, by genetically modifying the infectious cDNA clones to deliver additional viral antigens, thereby generating an immune response against PRRSV or other significant swine diseases in vaccinated pigs.

The North American strain of Porcine Reproductive and Respiratory Syndrome Virus ("PRRSV") viral clones employed in the present invention are isolated polynucleotides comprising infectious cDNA. An "isolated polynucleotide" is a polynucleotide that is generated from PRRSV viral genomic RNA via in vitro techniques. The term encompasses, for example, cDNA resulting from the reverse transcription of genomic RNA, vectors incorporating such cDNA, cDNA fragments produced by RT-PCR or restriction endonuclease digestion and recombinant nucleotide sequences that contain synthetic coding or non-coding genetic tags or a hybrid gene, i.e., a foreign gene encoding a marker protein. A "vector" is any polynucleotide entity capable of being replicated by standard cloning techniques.

Infectious cDNA clones transcribed in vitro by T7 polymerase or in vivo by host cell RNA polymerase are capable of completing the viral infectious cycle in host cells. "Infectious cDNA" as the term is used herein, refers to isolated cDNA that is capable of inducing cytopathic effect ("CPE") upon introduction into host cells. As used herein, "CPE" or "cytopathic effect" refers to observable changes in cell monolayers in vitro that indicate that viral replication has taken place. Suitably, newly generated viruses have growth kinetics similar to parental virus strains.

As used herein, "host cells" include both permissive and susceptible cells. "Permissive cells" are cells which can be used by the virus to replicate and produce viral particles upon introduction of viral RNA or infectious cDNA. Permissive cells may or may not have a cell surface receptor for the virus. "Susceptible cells," on the other hand, are cells bearing surface receptors for the virus, and which can by used by the virus to complete multiple cycles of proliferation and infection. Examples of suitable host cells include, but are not limited to, simian cell lines and porcine cells. Simian kidney cell lines are suitable host cells for in vitro applications. One such line, African Green Monkey continuous cell line MA-104, is commercially available. PRRSV exhibits tropism for lung alveolar macrophages in vivo.

In accordance with the present invention, viruses can be generated by transfecting permissive cells with infectious cDNA or with in vitro synthesized RNA from purified plasmid cDNA using prokaryotic promoters (such as T7 polymerase), or can be directly generated in vivo upon introduction of infectious cDNA via incorporation of eukaryotic promoters such as the CMV promoter. For in vitro methodologies, uptake of recombinant nucleic acid sequences into permissive cells can be achieved by a variety of known methods, such as, for example, by transfection. Suitable transfection methods include, but are not limited to, calcium phosphate coprecipitation, administering a complex of cationic liposomes, electroporation, receptor-mediated endocytosis and particle-mediated gene transfer.

Construction of Full-Length cDNA Clones of PRRSV

Described herein are full-length cDNA clones of North American PRRSV constructed in accordance with the present invention. In certain embodiments, infectious cDNA clones are prepared by first isolating and reverse-transcribing the genomic RNA of a field isolate of North American PRRSV that has been serially passaged in vitro. A preferred reverse transcription method known in the art is RT-PCR. Suitable oligonucleotide primers for RT-PCR can be designed using any known PRRSV strain sequences. Suitable primers designed using PRRSV strain SP (GenBank accession # AF184212) and/or PRRSV strain VR-2332 (GenBank accession # U87932) are shown in Table 1.

TABLE 1

Oligonucleotides used for RT-PCR, mutagenesis and Northern blotting

| Designation | SEQ ID NO: | Sequence | Position |
|---|---|---|---|
| RT-PCR | | | |
| STL | 2 | Acatgc<u>atgctaatacgactcactata</u>ggTATGACGTATAGGTGTTGGC | 1 |
| SL | 3 | acagcatgcgATGACGTATAGGTGTTGGCTCTATGCC | 1 |
| Qvt | 4 | gagtgacgaggactcgagcgcattaaTTTTTTTTTTTTTT | 15521 |
| SF797 | 5 | CCTCGTGGCGGGGATGAAGTGA | 797 |
| SR2573 | 6 | CTGCCCAGGCCATCATGTCCGAAGTC | 2573 |
| SF4344 | 7 | GCCCCGTCGGTCTCAGTCTTGCCATTTTT | 4344 |
| SR6589 | 8 | ACCGAGGCTGTAAAAGGCAAGTGACC | 6589 |
| SF7682 | 9 | CTTTCCGTTGAGCAGGCCCTTGGTATGA | 7682 |
| SR9573 | 10 | GTACCCGCACACTCTCGACTTCTTCCCCTCAT | 9573 |
| SF11210 | 11 | TCGTCCTATCCATGAGTATAGCCGCGC | 11210 |
| SF13016 | 12 | CAGCGCTACGAACCTGGCAAGGT | 13016 |
| SR13334 | 13 | TTGCCGCCGTCGACTTGATGCTGGTAAT | 13334 |
| SR15497 | 14 | CAATTAAATCTTACCCCCACACGGTCG | 15497 |
| Mutagenesis | | | |
| PSA2F | 15 | ttaattaatttaaatggcgcgccAATGAAATGGGTCCATGC | 12182 |
| PSA1R | 16 | ggcgcgccatttaaattaattaaTCAATTCAGGCCTAAAGTTGG | 12181 |
| APSD2 | 17 | atttaaattaattaaggcgcgccCACGCTGTCTCGCATTAGT | 12358 |
| SPAD2 | 18 | ggcgcgcccttaattaatttaaaTGTATCGCGGTGCAAACCG | 12583 |
| APSD4 | 19 | ggcgcgcccttaattaatttaaaTATAATTCTCATCTGTCAC | 13619 |
| SPAD4 | 20 | atttaaattaattaaggcgcgccCGATCAGTGCGGCTGCTC | 13793 |
| NDUF | 21 | AGCATGATGGGCTGGCATatgTCTTGAGGC | 15363 |
| NDUR | 22 | GCCTCAAGAtagATGCCAGCCCATCATGCT | 15389 |
| MLU5F | 23 | TGTCCTGGCGCTACgCgTGCACCAGATACA | 14291 |
| MLU5 | 24 | TGTATCTGGTGcAcGTAGCGCCAGGACA | 14320 |
| UASF | 25 | gggcgcgccATTCTTGAGGCATCTCAGTGTTTTG | 15379 |
| UPR | 26 | cttaattaaATCATGCTGTGGTGATGCTG | 15370 |
| PCPF | 27 | ccttaattaaTGACGTATCCAGGGAGGCG | PCV II |
| PCAR | 28 | aggcgcgccTTAGGGTTTAAGTGGGGGGTCTTTAAG | PCV II |

The designation of the primers in Table 1 includes a genomic position correlating to the position of the first 5' nucleotide in the full-length genomic sequences. The use of lowercase signifies non-viral sequence. Underlined sequences represent T7 promoter sequences. Anchor primer Qvt (SEQ ID NO: 4) contains Vsp I and Xho I recognition sequences which may be used for linearization of the plasmid with only two or 12 nonviral nucleotides beyond the authentic poly(A) stretch. "SF" indicates the oligonucleotide is a forward primer; "SR" indicates a reverse primer.

Some embodiments of the invention include genetic modifications of the infectious cDNA sequence, as further discussed below. For these embodiments, primers containing desired genetic mutations are listed in the lower panel of Table 1. Designations ending in "F" denote a forward primer, and those ending in "R" denote a reverse primer. SEQ ID NOS: 27 and 28 are suitably used to amplify the capsid gene of PCV II.

Figure 2:
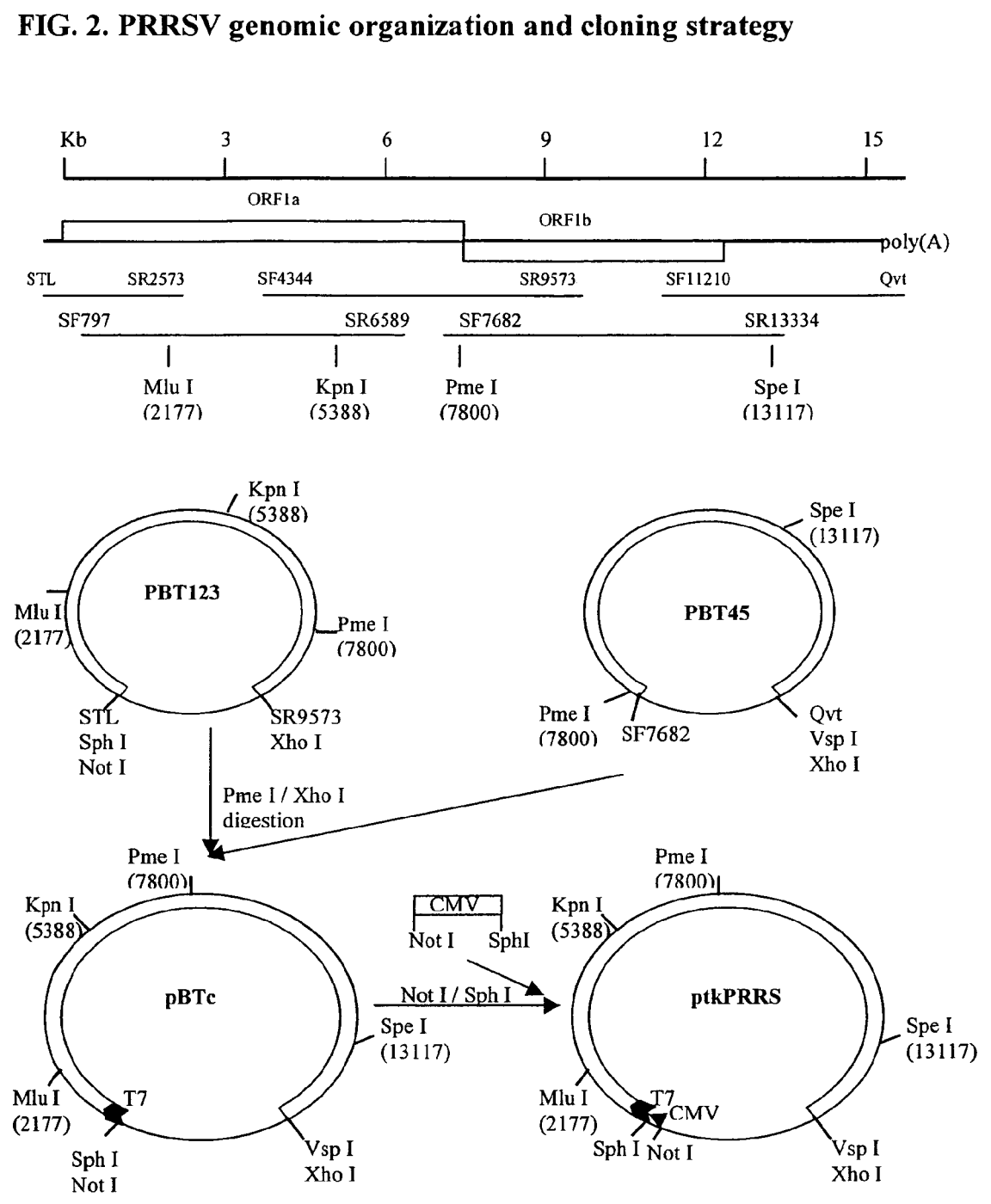

In one embodiment, high fidelity long RT-PCR is employed to produce primary cDNAs. One suitable overall cDNA preparation strategy is depicted in FIG. 2. Suitably, first-strand cDNA is synthesized from purified viral RNA with anchor poly(T) Qvt (SEQ ID NO: 4) as primer. Next, additional primers shown in Table 1 can be used to prepare primary fragments via PCR amplification. As will be understood in the art, any number of primary fragments can be generated. Preferably, about 3 to about 10 primary fragments are generated. As shown in the exemplified strategy depicted in FIG. 2, five primary fragments are generated. These primary fragments (designated TB1, TB2, TB3, TB4 and TB5 in FIG. 2) are then cloned using suitable vectors such as pZERO-Blunt and/or pCR-XL using the TOPO-cloning kit (Invitrogen, Carlsbad, Calif.) to produce primary clones.

Intermediate clones are then produced from the primary clones. In the exemplified method depicted in FIG. 2, TB2 and TB3 are combined via ligation and subsequently combined with TB1 to obtain intermediate clone pB123 of the 5' half of the genome. The 3' clone, designated pBT45, is constructed from fragments TB4 and TB5.

The intermediate vectors are further combined into a full-length PRRSV cDNA. The full-length cDNA clone depicted in FIG. 2, designated pBTc, is controlled by a T7 promoter located immediately upstream of the 5' UTR. To increase in vitro RNA transcription efficiency, two nonviral Gs are suitably interposed between the leader sequence and the T7 promoter sequence in pBTc. To allow transcription in vivo, ptkPRRS is suitably constructed based on pBTc by inserting a eukaryotic CMV (cytomegalovirus) promoter immediately upstream of the T7 promoter.

As will be appreciated by those of skill in the art, although the invention has been exemplified using particular vectors, any suitable vector systems may be used in the practice of the present invention. Suitable vectors for use with primary and intermediate clones include, but are not limited to, commercially available vectors such as pCR-ZERO Blunt, pCR-XL-TOPO, pBR322 (Invitrogen, Carlsbad, Calif.) and pUC19 (Promega, Madison, Wis.). High-copy phagemids such as pBluescript SK(+)™ (Stratagene Inc., La Jolla, Calif.) are suitable for cloning full-length infectious PRRSV cDNA.

Suitable infectious cDNA clones of the invention have at least about 80% nucleic acid sequence identity, preferably at least about 85% nucleic acid sequence identity, more preferably at least about 90% nucleic acid sequence identity, even more preferably at least about 95% nucleic acid sequence identity and yet more preferably at least about 98% nucleic acid sequence identity with SEQ ID NO: 1. "Percent (%) nucleic acid sequence identity" with respect to the PRRSV sequence identified herein is defined as the percentage of nucleotides in a candidate sequence that are identical with the nucleotides in a reference sequence after aligning and introducing gaps, if necessary, to achieve the maximum percent sequence identity. Alignment for purposes of determining percent nucleic acid sequence identity can be achieved in various ways that are within the skill in the art, for instance, using publicly available computer software such as ALIGN™ or DNASTAR™ software. Appropriate parameters for measuring alignment, including any algorithms needed to achieve maximal alignment over the full length of the sequences being compared, are known.

Genetic and Immunologic Modification of PRRSV

As will be understood by those of skill in the art, genetic modification of PRRSV cDNA of the invention will be useful as a means of differentiating engineered PRRSV cDNA from that of field isolates or commercial vaccine strains. In one embodiment, infectious cDNA clones are genetically modified by changing at least one nucleotide in at least one structural protein coding region, and/or at least one noncoding region. Genetic modification provides a suitable means of "marking" the engineered cDNAs for later identification via sequencing, PCR, restriction analysis and/or other methods of genetic identification known to those of skill in the art.

As used herein, "genetic modification" or "mutation" refers to methods of altering the sequence of nucleotides from those in a parent or reference sequence via deletion, substitution or insertion of one or more nucleotides. As contemplated by the invention, mutations may be in-frame, conservative or non-conservative, silent or non-silent. The phrase "attenuating mutation," means a nucleotide mutation or an amino acid coded by such a mutation which results in a decreased probability of disease in a host in accordance with standard terminology in the art. As used herein, "attenuating mutations" exclude mutations that are lethal to the virus. The phrase "silent mutation" refers to mutations in the cDNA coding sequence that do not produce mutations in the corresponding amino acid sequences as transcribed and translated therefrom. The phrase "degenerate" refers to sequences containing silent mutations.

Suitably, genetic modifications can be introduced in ORFs 5 and 7 without modifying the ability of the cDNA clones to produce infectious viral particles in a host cell. Such clones retain the infectivity of the parent and can be differentiated by molecular methods, including but not limited to, sequencing and restriction enzyme digestion followed by known visualization techniques.

In other embodiments, foreign nucleic acid sequences are inserted into the viral genome to create immunologic markers for recombinant viruses produced using isolated cDNAs constructed according to the present invention. As used herein, "foreign nucleic acids" include polynucleotide sequences that are neither native nor complementary to native sequences of the virus. Suitable foreign nucleic acids useful in practicing the present invention include polylinker sequences, coding sequences of marking polypeptides and open reading frames or partial open reading frames encoding immunologic peptides of any porcine virus for which it is desirable to induce an immune response in pigs. For example, as described below, the capsid gene of Porcine Circovirus Type II is suitably inserted in the PRRSV cDNA clones of the invention. Another example of a suitable gene is the hemagglutinin (HA) protein of Swine Influenza virus.

Suitable sites for the insertion of foreign coding sequences include immediately upstream of the ORF 2 region and/or at the beginning of the 3'-untranslated region of the viral genomic RNA. Such recombinant viruses retain their infectivity and thereby provide a foundation for further development of cDNA clones as an expression vector for the construction of genetically and/or immunologically marked recombinant vaccines.

The term "genetically marked," where used herein, refers to a genetically modified PRRSV cDNA or RNA sequence which can be identified by isolation of the sequence followed by sequencing or restriction enzyme digestion followed by fragment visualization techniques, well-known in the art, to allow identification of the marked sequence. Suitable embodiments include genetically marked PRRSV comprising an Mlu I site introduced by substitution in ORF 5, an Nde I site introduced by insertion in the 3' UTR, Pac I, Swa I, Asc I or Vsp I sites introduced by insertion at the junction of ORF 1 and ORF 2, or the deletion of sequences in the 3' end of the ORF 7, and 5' part of ORF 2 or the middle of ORF 4.

The terms "immunologically marked," and "antigenetically marked," where used herein, refer to genetically modified polypeptides comprising a PRRSV polypeptide, or domain sequence thereof, fused to a "marking polypeptide." The "marking polypeptide" comprises sufficient amino acid residues to provide an epitope against which an antibody may be made, or which can be identified by some other agent, yet is short enough that it does not interfere with the infectivity or activity of the virus. Suitable marking polypeptides generally comprise at least six amino acid residues and usually between about 8 to about 100 amino acid residues, preferably comprising between about 10 to about 50 residues.

Compositions

Compositions may be produced in accordance with the invention. Suitably, such compositions may be administered to animal subjects as a vaccine. As used herein, "vaccine" refers to a composition which, when administered to a subject, induces cellular or humoral immune responses. Such compositions may or may not be immunoprotective.

Suitable compositions comprise infectious PRRSV cDNA produced according to the invention or RNA or antigenic peptides produced in vitro from infectious PRRSV cDNA. Vaccine compositions can be produced either with or without genetic or immunologic mutations. Also suitable for use in compositions are whole live, attenuated or killed virus produced using infectious cDNAs of the invention. Vaccine compositions may include an aqueous medium, pharmaceutically acceptable inert excipients such as lactose, starch, calcium carbonate, and sodium citrate formed into tablets, capsules, or the like. Vaccine compositions may also include an adjuvant, for example, Freund's adjuvant. Vaccines may be administered alone or in combination with a pharmaceutical carrier that is suitable for administration to swine. Vaccines may be delivered orally, parenterally, intramuscularly, intranasally or intravenously. Oral delivery may encompass, for example, adding the compositions to the feed or drink of the animals. Factors bearing on the vaccine dosage include, for example, the weight and age of the pig. For purposes of parenteral, intramuscular, intranasal or intravenous administration, the vaccine compositions can be combined with known pharmaceutically acceptable carriers such as saline solution, water, propylene glycol, or triacetin. Compositions for parenteral or intravenous delivery may also include emulsifying or suspending agents or diluents to control the delivery and dose amount of the vaccine.

EXAMPLES

The present invention may be better understood with reference to the following examples. These examples are intended to be representative of specific embodiments of the invention, and are not intended to limit the scope of the invention.

Methods

Isolation of PRRSV. A field isolate of porcine reproductive and respiratory syndrome virus was amplified by serial passage on MA-104 cells, maintained in essential medium with Eagle's salts (EMEM, Gibco BRL) with 2% fetal bovine serum (FBS, Gibco BRL). The supernatant of the infected cells was harvested 4 to 5 days post-inoculation, when about 80% of the cells detached from the culture surface. The harvested material was stored at −70° C. as viral stocks.

RT-PCR amplification of viral cDNA. Viral RNA was purified using the QIAamp viral RNA isolation kit (QIAgen Inc., Valencia, Calif.) in accordance with the manufacturer's instructions. Reverse transcriptase (RT) Superscript II (Gibco BRL) was used to synthesize the first-stranded cDNA from the viral RNA, with hexamers or Qvt as primers, according to the manufacturer's instructions. Oligonucleotide primers, shown in Table 1, were designed based on available GenBank sequences # AF184212 and # U87932.

PLATINUM™ High Fidelity DNA polymerase (Gibco™, Carlsbad, Calif.) was used for PCR amplification of the cDNA fragments. Primers shown in Table 1 were added to 2 microliters of the RT reaction mixture. A normal PCR reaction included one cycle of 95° C. for 2 minutes, followed by 30 cycles of 95° C. for 15 seconds, 64° C. for 30 seconds, 68° C. for 1 minute per kilobase pair, and a final polish by incubation at 68° C. for 10 minutes. PCR products were identified by electrophoresis on a 1% agarose gel. DNA bands corresponding to viral cDNA were purified using the QIAEX II gel-purification kit (QIAgen Inc., Valencia, Calif.) according to the manufacturer's instructions.

Cloning and nucleotide sequencing of cDNA. The gel-purified cDNA fragments were cloned into the pCR™-ZeroBlunt-TOPO system (Invitrogen, CA) in accordance with the provider's instructions. Positive clones were first screened by agarose gel electrophoresis of the plasmids isolated with QIAprep™ Miniprep Spin Kit (QIAgen Inc., Valencia, Calif.), followed by restriction endonuclease digestion and/or nucleic acid sequencing. Restriction endonucleases and other DNA modifying enzymes were purchased from commercial sources (Promega, Madison, Wis.; New England Biolabs, Mass.), and used in accordance with the manufacturer's instructions. Nucleotide sequencing of the plasmids and/or PCR fragments was performed using an ABI 377 automatic sequencer in accordance with the instructions of the manufacturer. In addition to the primers listed in Table 1, additional sense or anti-sense sequencing primers specific for North American PRRSV genomic RNA were synthesized using standard techniques. The resulting sequences were analyzed using OMEGA™ 2.0 software (GCG Inc., Madison, Wis.) and LASERGENE™ Package (DNAstar Inc., WI).

Construction of full-length cDNA clones. PCR amplification was conducted to obtain DNA fragments TB1 (with primer pair STL/SR2573), TB2 (SF797/SR6589), TB3 (SF4344/SR9573), TB4 (SF7682/SR13334), and TB5 (SF11210/Qvt), followed by cloning into plasmid vector pZERO-Blunt and/or pCR-XL using the TOPO™-cloning kit (Invitrogen). A series of subcloning steps were carried out using unique restriction endonuclease cleavage sites in the targeted regions. Enzyme-restricted, gel-purified DNA fragments were ligated using 5-minute ligation kit (Invitrogen, Carlsbad, Calif.) and TOP10™ competent cells (Invitrogen) were transformed with the ligation mixture. In a first step, fragments TB2 and TB3 were connected via a restriction endonuclease Kpn I site at nucleotide (nt) position 5388 of the full-length genome. Subsequently, a unique Mlu I site at 2177 was utilized to obtain clone pBT123, representing the 5' half of the genome. The 3' clone, designated pBT45, was constructed by utilizing a Spe I site at nucleotide position 13117. Finally, the two plasmids were connected via a unique Pme I site at nucleotide position 7800 and cloned into pBluescript SK(+) vector (Stratagene). The full-length cDNA clone, pBTc, is controlled by a T7 promoter sequence located immediately upstream of the first nucleotide of the 5' UTR. To increase in vitro RNA transcription efficiency, two nonviral nucleotides Gs were added between the leader sequence and T7 promoter.

To construct a potentially infectious DNA, the eukaryotic cytomegalovirus (CMV) promoter was amplified from pCMV-Script (Stratagene, La Jolla, Calif.) template with Not I and Sph I sites flanking the 5' and 3' CMV promoter, respectively. The amplified CMV promoter sequence was inserted into the pBTc recipient plasmid after double digestion with Not I and Sph I such that the transcriptional start of the CMV promoter was located immediately upstream of the T7 promoter. Following transformation of E. coli TOP10 competent cells, a full-length clone driven by both eukaryotic and prokaryotic promoters was generated and designated as ptkPRRS.

To increase eukaryotic promoter efficiency of ptkPRRS, the CMV promoter start site was directly linked to the first nucleotide of the PRRSV sequence by eliminating the T7 promoter sequence. PCR with SL/SR 2537 was conducted with ptkPRRS as template. Following digestion with Sph I/Mlu I, the amplified fragment was inserted to the corresponding sites in pBTc, forming a clone of pMBC directly driven by CMV promoter. The full-length clone can be linearized by utilizing Vsp I or Xho I sites, introduced during construction using anchor primer Qvt (SEQ ID NO: 4).

Mutagenesis of full-length cDNA clones. To introduce genetic and/or antigenic makers into the PRRSV cDNA clone, a variety of mutations were conducted by using a slightly modified Quikchange Mutagenesis protocol (Stratagene, LaJolla, Calif.) with the 3' half of pBT45 as the template. FIG. 1 summarizes genetic modifications of the infectious cDNA clone. Two nucleotides at genomic position 14305 and 14307 were substituted to G from the original T and A, respectively, forming clone pM5CE, which contains a new Mlu I restriction endonuclease site. For mutations in the 3' UTR, pNUa and pUPS were generated by inserting Nde I and Pac I/Asc I sites, respectively, the latter containing a deletion of the first 7 base pairs of the 3' UTR. For insertion of longer genetic markers, a polylinker containing PacI/Swa I/Asc I sites was inserted between ORFs 1 and 2 to generate pCTSA2. The capsid gene of PCV type II was amplified by conducting PCR such that flanking Pac I and Asc I recognition sequences were added, and was then inserted into the corresponding sites of pCTSA2 to generate pCPV2. Plasmid pSD2 was a deletion mutant containing deletion of the 5' part of the ORF 2 coding region, while pSD4 habouring deletion of the middle part of the ORF 4.

To perform mutagenesis, high fidelity PCR amplification was carried out with corresponding primer pairs (Table 1) containing desired mutations as summarized in FIG. 1. A typical thermal cycling comprised denaturing at 95° C. for 5 minutes, followed by 18 cycles of denaturation at 95° C. for 30 seconds, annealing at 55° C. for 30 seconds, and extension at 68° C. for 20 minutes. The amplified products were further polished at 68° C. for 10 minutes, followed by salking at 4° C. until further treatment. To eliminate the template plasmid, 50 units of Dpn I was added to 50 microliters of PCR reaction mixture and incubated at 37° C. for at least 4 hours. For mutagenesis consisting of less than five base pair changes in the middle of the primer, 2 microliters of Dpn I-digested mixture was directly used to transform E. coli TOP 10 cells. For mutations involving longer insertion or deletion with the desired nucleotide changes located at the 5' end of the primer (Table 1), the Dpn I-treated reaction was purified using QIAquick PCR Cleanup kit (QIAgen) and reconstituted in 50 μl of nuclease-free water. The purified products were further digested at 25° C. for 2 hours with Swa I, one of the three, along with Pac I and Asc I, restriction enzymes having recognition sequences in the synthetic linker PSA. The digested mixture was purified as described above, followed by inactivation of Swa I at 65° C. for 15 minutes. The purified DNA was self-ligated by T4 DNA ligase (Invitrogen) at room temperature for 10 minutes, and then transformed into TOP 10 competent cells. The plasmids were subjected to restriction enzyme mapping and nucleotide sequencing for the desired mutation. Subsequently, the mutated plasmid was digested with Pme I and Xho I and inserted into similarly treated pBT123, as outlined in FIG. 2. As a result, a variety of mutants were constructed based on the location of the mutation (FIG. 1).

Transcription and transfection of the full-length cDNA clones with or without genetic modifications. RNA transcripts were synthesized in vitro by T7 RNA polymerase provided in the mMessage mMachine kit (Ambion Inc., Austin, Tex.) with about 1 microgram of VspI-linearized DNA template. After transcription, the DNA template molecules were eliminated by RNase-free DNase I digestion at 37° C. for 20 minutes. The synthesized RNAs were either used immediately or stored at −80° C. after identification by RNA agarose gel electrophoresis. One microgram of in vitro-produced RNA transcripts or plasmid DNA driven by CMV promoter was transfected into MA-104 cell monolayers in 6-well-plates, using DMRIE-C tranfection reagent (Gibco BRL) according to the instructions provided by the manufacturer. The transfection media was replaced with EMEM containing 2% FBS at 4 hours post transfection and further incubated at 37° C. in the presence of 5% $CO_2$ for 24 hours. 100 micoliters of the transfection supernatant was transferred to fresh MA-104 cells in a 6-well-plate. Three ml of EMEM containing 2% FBS was added after 1 hour adsorption at room temperature and incubation as described above. The culture supernatants, harvested at 4 or 5 days post inoculation when 80% of CPE developed, were stored at −80° C. until further use.

Genetic identification of the mutated genomic regions. To investigate whether the RNA- or plasmid-generated virus contained the engineered mutation, viral genomic RNA was isolated as described above. After synthesis of first-strand cDNA using Qvt as primer with Superscript II reverse transcriptase, PCR was conducted with primer pairs SF11210/SR 13334 for mutations in ranging from end of ORF1 thorough ORF3, while primer pair SF13016/SR15497 was used for downstream mutations. After purification with QIAquick PCR cleanup kit, PCR products were subjected to restriction endonuclease digestion followed by agarose gel electrophoresis analysis. The PCR products were further analyzed by nucleotide sequencing using a primer in the vicinity of the mutated sequences, followed by sequence comparison by computer analysis.

Northern Blot analysis of RNA profiles. For longer non-viral sequence insertion recombinant viruses, the retention of engineered genetic markers was further investigated by RNA blot analysis. Total cellular RNAs were prepared from virus- or mock-infected cells at 36 hours post inoculation at 0.5 MOI, using QIAgen RNeasy kit (QIAgen). Ten micrograms of total RNAs were separated on formaldehyde-denatured RNA gel and transferred to a nylon membrane. Anti-sense oligonucleotides PSAIR and PCAR (Table 1), were 3' end labeled with digoxigenin-11-2',3'-dideoxy-uridine-5'-triphosphate (DIG-11-ddUTP, Roche) by using terminal dideoxylnucleotide transferase (TdT, New England Biolabs) according to the supplier's instructions. The hybridization was conducted at 42° C. in ULTRAhyb-Oligo solution (Ambion) with the NorthernMax blotting kit (Ambion). After low and high stringency hybridization washes at 42° C. twice for 30 minutes, the colored hybridization signal was developed using the DIG Nucelic Acid Detection Kit (Roche).

Protein expression of the recombinant viruses. To investigate whether the transfected RNA or cDNA were capable of expressing authentic viral protein, a direct immunofluroscence assay was employed to detect the ORF 7-encoded Nucelocapsid (N) protein with monoclonal antibody conjugate SR30-F (Rural Technologies Inc., IA). To test whether the inserted capsid gene (ORF2) of porcine circle virus type II (PCV II), was expressed, an indirect immunofluroscence assay was conducted with primary anti-PCV II genotic pig serum and goat anti-porcine antibody FITC conjugate (191 IF, USDA-NVSL. Briefly, monolayers of MA-104 cells in four-well slide chambers (Nalgene) were infected at 0.1 MOI and fixed with a 1:1 mixture of methanol and acetone for 15 minutes. The fixed slide was incubated with anti-PCV II gnotobiotic serum for 30 minutes at 37° C., followed by staining with a secondary goat anti-porcine antibody conjugate. Unbound antibodies were washed off using 3 PBS flushes.

The use of recombinant virus as a vaccine candidate in pigs. To identify potential vaccine candidates, transfectant viruses were investigated for the ability to replicate in vivo and generate an immune response in inoculated pigs. Briefly, $1 \times 10^5$ PFU of viruses were suspended in 0.5 ml of EMEM (Invitrogen) and were intramuscularly inoculated into three two-month old pigs. Two additional pigs were inoculated with 0.5 ml of EMEM as negative controls. The pigs were bled at weekly intervals for two months post-inoculation. The pigs were also observed for PRRS clinical signs and overall growth status for 4 months post-inoculation. Serum samples were tested both for the presence of viral RNA and virus particles. Viral RNA was detected using RT-PCR with primer pair SF11210/SR 13334. Virus particles were detected by inoculating either 200 or 500 microliters of serum on MA-104 cells cultured in 6-well plates. In addition, a standard ELISA assay was used to determine PRRSV-specific antibody levels in inoculated and control pigs.

Results

Construction of full-length cDNA clones with or without mutations. Because all North American strains of PRRSV share at least 90% of nucleotide sequence identity, high-fidelity long PCR was used to amplify the cDNA of a field isolate that had been adapted on MA-104 cell culture for 58 passages. The primers listed in Table 1 were synthesized based on a consensus sequence incorporating available PRRSV sequences in GenBank. Included were accession numbers AF184212 and U87392. The RT-PCR product sequences were analyzed based on which intermediate cDNA clones were constructed. As shown in FIG. 2, pBT123 and pBT45, representing 5' and 3' halves of the cDNA clone, respectively, were connected via a unique Pme I site in the middle of the PRRSV genomic cDNA to generate the original full-length cDNA clone pBTc driven by the T7 promoter. Utilizing Not I and Sph I restriction sites preceding the T7 promoter sequence, the CMV promoter was inserted such that the transcription start of the CMV element was directly fused with the 5' end of the T7 promoter. This formed a dual promoter-driven full-length cDNA which was designated ptkPRRS. To produce eukaryotic-promoter-controlled clone pMBC, the T7 promoter was eliminated by replacing the Sph I/Mlu I fragment of pBTc with a PCR fragment in which Sph I was directly fused to the first base of the viral sequence.

Mutagenesis of the full-length cDNA clone was conducted using cDNA clone pBT45 and the QuikChnage XL™ mutagenesis system (Strategene) as described above. To generate substitution mutant pM5CE, the mutated pBT45 plasmid was used to replace the Pme I/Xho I fragment in ptkPRRS. The resulting mutant includes a substitution of two nucleotides to G from the original T at position 14305 and A at 14307, thus creating a new Mlu I cleavage site.

Two regions, the 3' UTR and junction between ORFs 1 and 2, were used to create genetic tag insertion mutants. The 5' end of the 3' UTR was tagged by inserting three nucleotides, ATG, at nucleotide position 15382 to generate mutant plasmid pNUa, which contained a new Nde I site. In addition, a polylinker consisting of restriction sites Pac I and Asc I was inserted in this region to form mutant plasmid pUPS4, which also contains a deletion of 7 nucleotides at nucleotide positions 15369-15375.

The noncoding region between the start of ORF 2 and the stop of the ORF 1b (between nucleotides 12181-12182) was used as a site for the insertion of a polylinker to facilitate nonviral sequence insertions. Mutant plasmid pCTSA incorporates a 23 nucleotide insertion harboring restriction endonuclease cutting sites Pac I, Swa I and Asc I. To test the potential for foreign gene expression at this site, a PCR-amplified capsid gene of Porcine Circovirus Type II (PCV II) flanked by Pac I/Asc I sites was inserted in pCTSA to generate pCPV2.

Finally, extensive deletions were in ORF 2 and ORF 4 were made to form additional mutants. The mutant pSD21 contains a deletion from 12358 to 12583, while pSD47 harbors a deletion in the middle of the ORF 4 coding sequences from 13619-13793. The above-described mutagenesis strategies are summarized in FIG. 1.

To verify that the expected mutations resulted, nucleotide sequencing of ptkPRRS and the regions of mutations in mutant plasmids were conducted. Resultant sequences were assembled using SEQMAN software included in the Lasergene package (DNASTAR, Madison, Wis.). Nucleotide sequence analysis confirmed the presence of all engineered mutations. However, in addition to the deletion of seven nucleotides at the beginning of the 3' UTR, a deletion at position 15363 and a substitution (C to A) were also noted. It is believed that the additional mutations resulted from imprecise primer design. The additional mutations resulted in a frame-shift of the last 3 amino acids of the ORF 7 gene product. This frameshift did not impair virus replication.

In vitro-generated RNAs generated typical PRRSV CPE. Upon transcription of the full-length infectious cDNA, the resulting genomic RNA comprises 15521 nucleotides. The untranslated regions (UTR) at the 5' and 3' ends of the genome comprise nucleotides 1-191 and 15371-15521, respectively. The viral replicase complex, a series of proteolytic nonstructural proteins, is encoded by ORF 1a and 1b, with the latter translated by a −1 frame-shifting mechanism. ORF 1a is encoded by nucleotides 192-7798, while ORF1b is encoded by nucleotides 7797-12181. The structural proteins are encoded by ORF 2 (nucleotides 12183-12953), ORF 3 (nucleotides 12806-13570), ORF 4 (nucleotides 13351-13887), ORF 5 (nucleotides 13898-14500), ORF 6 (nucleotides 14485-15009) and ORF 7 (nucleotides 14999-15370).

To test the infectivity of the full-length cDNAs, in vitro transcripts with 5' caps were generated using pBTc linearized with Vsp I. As a negative noninfectious control, BTSX synthetic RNAs transcribed from pBTc with the Spe I/Xho I fragment encoding the main structural proteins and the 3' UTR deleted were also generated. Viral RNA purified with QIAgen Viral RNA kit was used as a positive control for RNA transfection of MA-104 or BHK-21 cells with DMRIE-C reagent (Invitrogen). Both the viral and synthetic BTc RNAs developed typical PRRSV CPE beginning at 2 or 3 days post transfection (dpt). By 4 days dpt, virtually all MA-104 cells were destroyed, and more than half of the BHK-21 cells were detached from the culture plate. Two hundred microliters of the transfection supernatants were then transferred to fresh MA-104 cells. For viral and BTc RNAs, CPE began at 2-3 days post inoculation, while BTSX RNAs did not show CPE in either the transfection plate or the transferred transfectant-infected cells. This experiment was repeated at least three times and the development of CPE induced by pBTc synthetic RNAs remained consistent, thereby demonstrating that pBTc is indeed an infectious cDNA clone of PRRSV. Not unexpectedly, the in vitro RNA transcripts from plasmid ptkPRRS were also infectious and developed CPE on MA-104 cells with the same growth kinetics as that of pBTc transcripts and parental viral genomic RNAs.

To investigate whether PRRS virus particles can be generated from the mutated full-length plasmid clones, RNAs were generated in vitro as described above and transfected into MA-104 cells. Twenty-four hours post transfection, supernatants were further transferred onto fresh MA-104 cells. RNA transcripts from mutants pM5CE, pNUa, pCTSA, and pUPS4 were infectious and developed CPE in both the transfected cells and the first passage of the transfectant supernatant on MA-104 cells at 2 or 3 days post treatment. However, the mutant RNAs with larger deletions in ORF2 (pSD21) and ORF4 (pSD47) did not generate CPE in either assay, even by 14 days post-treatment. These results demonstrated that full-length cDNA clones pBTc and ptkPRRS, and derivatives harboring minor mutations can mimic the infectious cycle of parental PRRSV. The non-infectivity of mutants pSD21 and pSD47 transcripts may reflect that the corresponding gene products serve essential functions of in the life cycle of PRRSV.

Infectivity of eukaryotic DNA promoter controlled plasmids. To test the potential of the infectious cDNA clones as a genetic vaccine, CMV promoter driven plasmid cDNAs were directly transfected into MA-104 cells. The cDNAs transfected included: 1) intact ptkPRRS driven by T7 and CMV promoters; 2) ptkPRRS linearized with Vsp I; 3) pMBC driven by the CMV promoter; and 4) pBTc driven by the T7 promoter as a control. All but pBTc resulted in CPE in transfected cells 7 days post transfection (dpt), somewhat slower than RNA transfections. Surprisingly, similar CPE development kinetics was observed for all cDNA preparations, including ptkPRRS linearized with Vsp I and pMBC, which driven by CMV promoter directly. Upon inoculation of fresh MA-104 cells with transfectant supernatants, CPE developed at the same pace as the parental virus and RNA transfectant viruses. Thus, the delay of the appearance of CPE upon cDNA transfection may reflect time needed for nuclear transcription and transportation of the RNAs to virus assembly factories located in cytoplasm. Nonetheless, these results demonstrated that both linear and circular eukaryotic CMV promoter-driven cDNAs were capable of generating authentic PRRSV CPE in vitro.

Identification of the genetic markers in the recovered transfectant viruses. To confirm that the transfectant viruses contained the expected mutation, RT-PCR was conducted as described above by using the transfectant viral RNA. RT-PCR with primer pairs SF11210/SR13334 or SF13016/SR15497 was conducted from viral RNAs purified from the supernatants of the transfectant virus cultures at passage 2. The purified amplification products were subjected to restriction endonuclease digestion with Mlu I for vptkRRS (lane 1) and vM5CE (lane 2), or Asc I for vCTSA (lane 4) and vBTc (lane 5). The results are shown in FIG. 3. Mlu I cut the PCR product from transfectant virus vM5CE (lane 2), but not that of vptkRRS (lane 1). In a similar manner, an Asc I site was detected from transfectant virus vCTSA (lane 4) but not the parental vBTc (lane 5).

PCR amplified products were further subjected to nucleotide sequencing and compared with both the plasmid mutants and the parental viral sequences. First-strand cDNA was synthesized using superscript II reverse transcriptase and an anti-sense anchor primer Qvt from the viral RNA, purified via QIAgen Viral RNA kit. PCR was conducted using the corresponding primer pairs covering the mutated regions of about 2 kb. The amplified PCR products were purified using QIAgen PCR cleanup kit and subjected to nucleotide sequence analysis using a Perkin-Elmer ABI 377 sequencer. As shown in sequence lineups in FIG. 4, the RT-PCR product nucleotide sequences of vM5CE, vNUa, vUPS4, and vCTSA each contains the expected mutations compared to their parental sequences, indicating that these mutant plasmid clones generated transfectant viruses. The lineups of the nucleotide sequences were done by using LASERGENE™ DNA package (DNASTAR, Madison, Wis.).

Surprisingly, vUPS4 was as infectious as the parental virus, despite the retention of serendipitous mutations at the end of ORF 7, indicating that these sequences encoding the nucleocapsid protein are non-essential for viral replication.

The restriction enzyme mapping and nucleotide sequencing results demonstrated that transfectant viruses were generated from the mutant plasmids, and that the infectious cDNA PRRSV clones can be utilized for engineering recombinant PRRSV containing desired genetic markers.

Expression of PCV capsid gene in PRRSV cDNA clone. To test the potential of infectious PRRSV cDNA as an expression vector for foreign genes of interest, recombinant plasmid pCPV2 was constructed by inserting the PCV II capsid gene into pCTSA2. To construct vCPV2, the RNA transcripts from pCPV2 were transfected into MA-104 cells and 200 microliters of the transfection supernatant was inoculated on fresh MA-104 cells. Both the initially transfected cells and first passage cells developed CPE at 3 days post treatment, one day later than parental pCTSA2 transcripts.

The resultant supernatants were further passaged on MA-104 cells four times. Supernatant from the fourth passage of the vCPV2 was used for RT-PCR amplification of the inserted region with primer pair SF11210/SR13334. The purified RT-PCR product was subjected to restriction enzyme mapping and nucleotide sequencing. As shown in FIG. 5A, both the amplified vCPV fragment (lanes 1 and 2) and the vCTSA2 parent (lanes 4 and 5) contained Asc I as well as Pac I sites. Double digestion (lane 2) of vCPV2 with Pac I and Asc I released a fragment about 300 bp in length which was barely seen yet could be confirmed by the sizes of the visible bands. Nucleotide sequencing results confirmed that a 315 bp sequence was inserted instead of the expected 703 bp PCV capsid gene. As shown if FIG. 5B, sequence lineups with the pCPV2 plasmid revealed that transfectant virus vCPV2 retained 115 and 207 nucleotides from the 5' and 3' end, respectively, with a 381 base deletion in the middle of the capsid gene. As a result, while the first 38 amino acid residues expressed authentic PCV protein, downstream residues were changed by frame shifting due to the deletion.

As shown in FIG. 5B and FIG. 5C, the stop codon of the PCV II gene was also mutated. In vCPV2, a TAA codon was changed to TCA while the plasmid pCPV contains the authentic PCV sequences. Not to be bound by theory, it is hypothesized that the inserted PCV sequence is expressed as part of fusion protein with the PRRSV ORF 2 glycoprotein. As shown in FIG. 5A, the N- and C-terminal ends of the PCV capsid gene are expressed with an internal deletion, indicating that up to 312 nucleotides of nonviral sequences can be expressed at the junction of ORFs 1 and 2. Nevertheless, it is possible that a larger capacity of a foreign gene insertion may yet exist at this site, because the PCV sequence may have been deleted as a result of a specific deleterious effect on the PRRSV infectious cycle.

Northern blotting showed that inserted sequences were expressed in subgenomic RNAs. To investigate whether the inserted CPV2 sequence, or the PSA linker, was expressed in the form of subgenomic mRNAs, Northern blotting analyses were conducted. Total cellular RNA from mock-, ptkPRRS-, and vCTSA-infected cells were blotted against using probe PSAIR (SEQ ID NO: 16) labeled with DIG-11-ddUTP. As shown in FIG. 6, vCTSA expressed the PSA linker at approximately mRNA2 in the parental virus (lane 1), which showed a weak hybridization signal. In addition, the PSAIR probe detected genomic RNA, which in turn confirmed that the PSA linker was inserted into the genome of vCTSA2 recombinant virus. The appearance of minor bands longer than mRNA2 was a typical phenomenon of PRRSV replication, (Yuan et al., Heteroclite subgenomic RNAs are produced in porcine reproductive and respiratory syndrome virus infection. Virology 275, 158-169 (2000)) and likely represented defective RNAs, or heteroclite RNAs.

The feasibility of expressing a foreign gene at the junction of ORFs 1 and 2 was further investigated by analyzing the genetic profile of vCPV2 transfectant virus infected cells. Total cellular RNAs were isolated with QIAgen RNAeasy Kit (QIAgen) from infected cells at 36 hours post infection. Denatured RNA gel electrophoresis and northern blotting were done using NorthenMax system (Ambion). Because of the PSA linker insertion in pCTSA, PSA1R (SEQ ID NO: 16) was Dig-11-ddUTP labeled and used as a probe against RNAs from cells infected by vCTSA (lane 2), ptkPRRS (lane 1), and mock-infected (lane 3). Based on the fact that the 3' end of the PCV capsid gene was expressed by the vCPV2 transfectant virus, the anti-sense primer used for amplification of PCV capsid gene, PCAR (SEQ ID NO: 28), was labeled with Dig-11-ddUTP for use as a probe against total cellular RNAs of cells infected by vCPV2 (lane 4) and ptkPRRS (lane 5). As shown in FIG. 6, the PCV sequence indeed presented as part of the viral genomic RNA and a subgenomic RNA similar to mRNA 2 in terms of the size in the cells infected by passage 4 of vCPV2 transfectant virus (lane 2). These results demonstrated that an infectious cDNA clone can be used to express foreign genes of interest.

The infectious cDNA generated viruses expressed PRRSV proteins and retained the antigenic marker. To confirm that the transfectant viruses capable of inducing CPE were indeed PRRSV-specific, a direct immunofluroscence assay was conducted The in vitro-transcribed RNAs from corresponding cDNA clones under control of T7 promoter were used for transfection of MA-104 cells, using DMRIE-C reagent according to the protocol of the supplier (Invitrogen, Carlsbad, Calif.). At 24 to 48 hours post transfection (hpt), 200 microlilters of the resultant supernatants were used to inoculate fresh MA-104 cells. At 48 hours post infection, the virus- or mock-infected cell monolayers were subjected to immunofluroscence assay using anti-PRRSV monoclonal antibody SR-30F, labeled with FITC. (Rural Technologies Inc. Ames, Iowa). As shown in FIG. 8, vptk-PRRS (Panel A), vCTSA (Panel B), and vCPV2 (Panel 3) stained positive, demonstrating that transfectant viruses mimic parental viral infection in MA-104 cell culture.

Cells infected by vCPV2 and ptkPRRS and mock infected cells were fixed with acetone at 5 days post infection (dpi) and subjected to an indirect immunofluroscence assay (IFA). After incubation with primary anti-PCV II antibody, goat anti-porcine serum-FITC conjugates were utilized to detect PCV II-specific protein expression. As shown in FIG. 9, Results for vCPV2 demonstrated that infectious cDNA-generated transfectant viruses can not only mimic virus infection, but are also suitably used for expression of genes of interest.

Vaccine candidacies of the recombinant PRRSV. To investigate whether transfectant viruses also micmic parental virus infection in vivo, $1 \times 10^5$ of vCTSA in 0.5 ml of EMEM were administered intramuscularly into 2-month old pigs. Serum samples were collected at weekly intervals until two months post inoculation, and tested for the presence of viral RNA, virus, and PRRSV-specific antibody. As shown in FIG. 7A, RT-PCR amplification results conducted using serum samples collected at day 7 (lanes 2, 4 and 6) and day 14 (lanes 3, 5 and 7) from 3 pigs revealed that viral RNAs were more abundant at 7 days post infection (dpi). However, no viral RNA was detected at 7 dpi for pig number 616 (lane 6).

Viral RNAs were isolated from 140 μl of serum from mock- or vCTSA-infected pigs, and subjected to RT-PCR with primers SF11210/SR13334. RT-PCR was also conducted with vCTSA viruses cultured in vitro. As shown in FIG. 7B, nucleotide sequencing of the purified PCR products deomstrated that the PSA linker, used as a genetic marker, was retained. These results indicate that vCTSA2 transfectant virus stably replicates in both in vitro and in vivo systems. All of the infected pig sera remained negative at all time points for PRRS virus isolation on. MA-104 cells throughout two further passages, indicating that the vCTSA virus was attenuated by the insertion of foreign sequence and/or a result of in vitro passage of the parental virus. Furthermore, no typical PRRS clinical signs were noticed and normal growth was noted for all inoculated pigs, indicating that the vCTSA2 viruses replicated, yet were attenuated, in the inoculated pigs. Furthermore, seroconversion was detected by ELISA assay (data not shown) at 3 weeks postinfection and maintained through the eighth week postinfection. Therefore, vCTSA seems to be an ideal genetically-tagged PRRS virus that is attenuated, yet stimulates at least humoral immune responses.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide comprising the nucleotide sequence of SEQ ID NO: 1 or a degenerate variant of SEQ ID NO: 1.

2. A vector comprising the polynucleotide of claim 1.

3. An isolated polynucleotide comprising a modified nucleotide sequence of SEQ ID NO:1, wherein the modified nucleotide sequence comprises a marker sequence.

4. The isolated polynucleotide of claim 3, wherein the marker sequence comprises a restriction enzyme recognition sequence or a polynucleotide sequence that encodes an immunologic polypeptide.

5. The isolated polynucleotide of claim 4, wherein the marker sequence encodes a porcine viral polypeptide.

6. The isolated polynucleotide of claim 5, wherein the porcine viral polypeptide comprises a capsid protein of Porcine Circovirus Type II or a hemagglutinin protein of Swine Influenza virus.

7. The isolated polynucleotide of claim 3, wherein the marker sequence comprises at least one foreign polynucleotide sequence inserted:

(a) between nucleotide positions 12181-12182 of SEQ ID NO: 1; or (b) between nucleotide positions 15382-15383 of SEQ ID NO: 1.

8. The isolated polynucleotide of claim 3, comprising a substitution at nucleotide position 14305 and position 14307 of SEQ ID NO: 1.

9. The isolated polynucleotide of claim 3, wherein at least one nucleotide is deleted:

(a) between nucleotide positions 15364-15370 of SEQ ID NO: 1; or (b) between nucleotide positions 15371-15375 of SEQ ID NO: 1.

* * * * *

SEQUENCE LISTING

```
<160> NUMBER OF SEQ ID NOS: 28

<210> SEQ ID NO 1
<211> LENGTH: 15543
<212> TYPE: DNA
<213> ORGANISM: Porcine reproductive and respiratory syndrome virus

<400> SEQUENCE: 1
tatgacgtat aggtgttggc tctatgcctt gacatttgta ttgtcaggag ctgtgatcat    60
```

| | |
|---|---|
| tgacacagcc caaagcttgc tgcacagaaa cacccttctg tgacagcctc cttcagggga | 120 |
| gtttaggggt ctgtccctag caccttgctt ccggagttgc actgctttac ggtctctcca | 180 |
| cccctttaac catgtctggg atacttgatc ggtgcacgtg taccccaat gccagggtgt | 240 |
| tcatggcgga gggccaagtc tactgcacac gatgcctcag tgcacggtct ctccttcctc | 300 |
| tgaatctcca agttcctgaa ctcggggtgc tgggcctatt ctataggccc gaagagccac | 360 |
| tccggtggac gttgccacgt gcattcccca ctgttgagtg ctccccgcc ggagcctgct | 420 |
| ggctttctgc catctttcca attgcacgaa tgaccagtgg aaatctgaac tttcaacaaa | 480 |
| gaatggtgcg ggtcgcagct gagctttaca gagccggcca gctcacccct gcagtcttga | 540 |
| agactctaca agtttatgaa cggggttgcc actggtaccc cattgttgga cctgttcctg | 600 |
| gagtggccgt ttatgccaac tccctacatg tgagtgataa acctttcccg ggagcaactc | 660 |
| acgtgttaac caacctgccg ctcccgcaga gacccaagcc tgatgatttt tgccccttttg | 720 |
| agtgtgctat ggctactgtc tatgacattg gtcatgacgc cgtcatgtat gtggccgaag | 780 |
| agaaagtctc ctgggcccct cgtggcgggg atgaagtgaa attcgaacct gtccccgggg | 840 |
| agttgaagtt gattgcgaac cgactccgca cctccttccc gccccaccac gcagtggaca | 900 |
| tgtctaagtt caccttcaca gcccctgggc gtggtgtttc tatgcgggtc gaacgccaac | 960 |
| acggctgcct ccccgctgac acagttcctg aaggcaactg ctggtggagc ttgttcaact | 1020 |
| tgctcccact ggaagttcag aacaaagaaa ttcgtcatgc cggccaattt ggctaccaga | 1080 |
| ctaagcatgg tgtctctggc aagtacctac agcggaggct gcaagttaat ggtcttcgag | 1140 |
| cagtaactga cctaaatgga cctatcgtcg tacagtgctt ctccgttaag gagagttgga | 1200 |
| tccgccactt gaaactggcg gaagaaccca gctaccctgg gtttgaggac ctcctcagaa | 1260 |
| taagggttga gcccaacacg tcgccattgg ctgacaagga tgaaaaaatt ttccggtttg | 1320 |
| gcaatcacaa gtggtatggc gctggaaaga gagcaaggaa agcacgctct agtgcgactg | 1380 |
| ctacagtcgc tggccgcgct ttgcccgttc gtgaaacccg gcaggtcgag gagcacgagg | 1440 |
| ttgccggcgc caacaaggct gagcacctca aacactactc cccgcctgcc gaagggaatt | 1500 |
| gtggttggca ctgcatttcc gccatcggca accggatgtt gaattccaaa tttgaaacca | 1560 |
| cccttcccga aagagtgaga cctccagatg actgggctac tgatgaggat cttgtgaatg | 1620 |
| ccatccaaat cctcagactc cctgcggcct tggacaggaa cggtgcttgt gctagcgcca | 1680 |
| agtacgtact taagctggaa ggtgagcatt ggactgtcac tgtgacccct gggatgtccc | 1740 |
| cttctttgct ccctcttgaa tgtgttcagg ctgttgcga cataagggc ggtcttggtt | 1800 |
| ccccagatgc agtcgaggtt ttcggatttg accctgcctg ccttgactgg ctggctgagg | 1860 |
| tgatgcactt gcctagcaat gccatcccag ccgctctggc cgaaatgtcc ggcgattcca | 1920 |
| atcgtccggc ttccccggtc accaccgtgt ggactgtttc gcagttctta gcccgccaca | 1980 |
| acggagggaa tcaccctgac caaatacgct tagggaaaat tatcagcctt tgtcaggtga | 2040 |
| ttgaggactg ctgctgttcc cagaacaaaa ccaaccgggt caccccggag gaggtcgcag | 2100 |
| caaagattga cctgtacctc cgtggtgcaa caatcttga agaatgcttg ccaggcttg | 2160 |
| agaaagcgcg cccgccacgc gtaatggaca cctcctttga ttgggatgtt gtgctccctg | 2220 |
| gggttgaggc ggcaactcaa acgaccgaac tgccccaagt caaccagtgt cgcgctctgg | 2280 |
| tccctgttgt gactcaaaag tccttggaca caactcggt ccctctgacc gccttttcac | 2340 |
| tggctaacta ctactaccgc gcgcaaggtg acgaagttcg tcaccgtgaa agactaacca | 2400 |
| ccgtgctctc taagttggaa ggggttgttc gagaagaata cgggctcatg ccaaccgggc | 2460 |

```
ctggtccacg gcccacactg ccacgcgggc tcgacgaact caaggaccag atggaggtgg    2520
acttgctgaa actggctaac gcccagatga cttcggacat gatggcctgg gcagtcgagc    2580
aggttgacct aaagacttgg gtcaagaact atccgcggtg acaccacca cctcctccgc    2640 caatagttca gcctcgaaaa acgaagcttg tcaagagctt accagagagc aagcctgttc    2700
ctgcaccgcg taggaaggtc aggtccgatt gtgactgccc cacccctatcg ggcaacaatc    2760 ttcctgacag ttgggaagat ttggctgttg gttgcccctc tgatctccct acctcacctg    2820
agccggtaac acctttgagt gagccggcat ctgtgtccgc accgcgacgc tcttttaggc    2880
cggtgaagcc tttgagtgaa ccagttccag tccctgcacc gcgcaagact gtgtcccgac    2940
cggcaacacc tctgagtgag ccgatccctg tgcccgcacc gcgacgcaag tttcagcagg    3000 tagaaaagt gaatccggcg gcggcaaccc tggcgtgcca agacgagttt ccagatttgt    3060
ctgcatcctc gcatactgaa tatgaggcgt ctccccttgt actaccgcag aacggggacg    3120
ttcttgaagt ggaggagcgg gaagctgagg aaatcctgag tggaatctca gacatactgg    3180
atgccatcaa accggcatct gcatcatcaa gcagctccct gtcaagtgtg gcgatcacac    3240
gcccgaaata ctcagctcaa gccatcattg actcgggtgg gccctacagc gggcatctcc    3300
aagaggtgaa ggaaacatgc ctaagcatca tgagtgaggc atgtgatgtg accaagcttg    3360
atgaccctgc cacgcaggaa tggctttctc gcatgtggga tagggtggac atgctgactt    3420
ggcgcaatac gtctgttcac caggcgtctc gcaccttgga cgacagattt aagtttctcc    3480
cgaagatgat acttgaaaca ccgccgccct acccgtgtgg gttcgtgatg atgcctcgca    3540
cacctgcacc ctccgtgggt gcggagagcg acctcactat tggctcagtc gctactgagg    3600
acgttccacg catcttcggg aaagtaaatg atgtctgcaa gatgatcgac cagagaccct    3660
tggtactctt tgaaaatgag ctggcagatg accaacctgc cagagatcct cggacatcat    3720
cgcagaggtt tgacgggagc acaccagctc cgcccgcagg cacggatggc accggtttgg    3780
cttcgggccc tggagtgaga gaagtggatt catgtgaggc gagctcaacc gagaaaaatg    3840 aacagcccctt cgtgttgaac ggcggcgcca gcacacaggc gtcaacgttt accaatttgc    3900
cgcctccagg cggtatagat gcgggcggga gtgggccgtt acaaacggtg cgaaagaagg    3960
ctgaacggtt ctttgaccta ctaagccgtc aggtttttaa tctcgtctcc catctccctg    4020
ttttcttctc acgccttttc aaacctggcg gtgactattc tccgggtgat tggggttttg    4080 cagctttac tttattgtgc ctcttttttgt gttacagtta cccggccttt ggtgctgttc    4140
ccctcttggg tgtatttttct gggtcttctc ggcgtgttcg aatgggggtt tttggctgct    4200
ggttggcttt tgctgttagt ctgttcaaac ctgtgtccga cccagtcggc gctgcttgtg    4260
aatttgattc gccagagtgt agaaacatcc ttcattcttt tgagcttctc aaaccttggg    4320
accctgttcg cggccttgtt gtgggccccg tcggtctcag tcttgccatt tttggcaggt    4380
tattgggcgg ggcacgccac atctggcact ttttgcttag gtttggcatt gttgcagatt    4440
gtatcttggc tggagcttat gtgctttctc aaggcaggtg taaaaagtgc tgggatcttt    4500
gtataagaac tgctcctaat gaggtcgcct ttaacgtgtt tcctttaca cgtgcgacca    4560 ggtcgtcact tatcgacctg tgcaatcggt tttgcgcgcc aaaaggtatg gaccccattt    4620
tcctcgccac tgggtggcgc gggtgctgga ccggccgaag ccccattgag caaccctctg    4680
aaaaacccat cgcgtttgcc cagttggatg aaaaaaagat tacggctagg actgtggtcg    4740
cccagcccta tgaccccaac caagctgtaa agtgcttgcg ggtattgcag gcgggcgggg    4800
```

```
tgatggtggc tgaggcagtc ccaaaagtgg tcaaagtttc tgctgttcca ttccgagccc    4860
ccttctttcc caccggagtg aaagttgatc ctgaatgcag gattgtggtt gaccccgaca    4920
ctttcactgc agccctccga tctggctact ccaccacaaa cctcgtcctt ggtgtggggg    4980
actttgccca gctgaatgga ttaaaaatca ggcaaatttc caagccttca gggggaggtc    5040
cacacctcat ggctgccctg catgttgctt gctctatggc tctgcacatg cttgttggga    5100
tttatgtgac tgctgtgggt tcttgcggca ccggcactaa cgatccgtgg tgcgccaacc    5160
cgtttgccgt ccctggctac ggacctggcc tctctgcac gtccagattg tgcatctccc    5220
aacatggcct taccctaccc ttgacagcac ttgtggcggg attcggcttt caggaaattg    5280
ccttggttat tttgattttt gtttctatcg gaggcatggc tcatagattg agttgcaagg    5340
ctgatatgct gtgtattttg tttgcaatcg ccagctatgt ttgggtacct cttacctggt    5400
tgctttgtgt gtttccttgc tggttgcgct gtttttcgtt gcaccccctc accatcctat    5460
ggttggtgtt tttcctgatt tctgtaaata tgccttcagg aatcttggcc ttggtgttgt    5520
tgatttctct ctggcttctt ggtcgttata ccaacgttgc cggtcttgtc actccctatg    5580
acattcatca ttacaccagt ggccccgcg gtgttgccgc cttggctacc gcaccagatg    5640
ggacctactt ggccgctgtc cgccgcgccg cgttgactgg tcgcaccatg ctgtttaccc    5700
cgtctcagct cgggtccctt cttgagggcg ctttcagaac tcgaaagccc tcactgaaca    5760
ccgttaatgt ggtcgggtcc tccatgggct ctggcggggt gttcaccatc gacgggaaaa    5820
ttaagtgcgt aactgctgca catgtcctta cgggtaattc agctagggtt ccgggggttg    5880
gcttcaatca aatgcttgac ttcgatgtga aggagactt cgccatagcc gattgcccag    5940
actggcaagg ggctgctccc aagacccaat tctgcgagga aggatggact ggccgggcct    6000
attggctaac gtcttctggt gtcgaacccg gcgtcattgg aaaaggattc gccttctgct    6060
tcaccgcgtg cggcgattcc ggatcccag taatcaccga ggccggcgag cttatcggcg    6120
ttcacacggg gtcaaataaa caaggaggag gcatcgtcac gcgcccctca ggccagtttt    6180
gtagtgtggc acccgtcaaa ttaagcgaac taagtgaatt cttttgcaggg cctaaggtcc    6240 cgctcggtga tgtgaaagtt ggcagccaca taattgaaga cgtaggcgag gtgccttcag    6300
atctttgcgc cttgcttgct gccaaaacctg aactggaagg aggcctctcc accgttcaac    6360
ttctgtgtgt gttttttcctc ctgtggagaa tgatgggaca tgcctggacg cccttggttg    6420
ccgtagggtt tttatcttg aatgaggtcc tcccagctgt cctggtccgg agtgtttttct    6480 cctttggaat gtttgtgcta tcctggctca caccatggtc tgcgcaagtt ctgatgatca    6540
ggcttctaac agcagctctt aacaggaata gatggtcact tgccttttac agcctcggtg    6600
caatgactgg ttttgtcgca gatctcgcgg ctactcaggg gtatccgttg caggcagtga    6660
tgagtttgag cacttatgca ttcctgcctc ggataatggt tgtgacttca ccagtcccag    6720
tggttgcgtg tggtgttgtg cacctacttg ccatcatttt gtacttgttt aagtaccgct    6780
gcctgcacaa catccttgtt ggcgatggag tgttctctgc ggctttcttc ctgcgatatt    6840
ttgccgaggg aaagttgagg gaggggggtgt cgcaatcctg cgggatgaat catgagtcac    6900
ttaccggtgc cctcgctatg agactcaatg acgaggactt ggatttcctc acgaaatgga    6960
ctgatttcaa gtgctttgtt tctgcgtcca acatgagaaa tgctgcgggc caattcatcg    7020
aggctgccta tgctaaagca cttagagtag aacttgccca gttggtgcag gttgataagg    7080 ttcgggtac tttggccaaa cttgaagctt tgccgacac cgtggcaccc caactctcgc    7140
ccggtgacat tgttgtcgct cttggccata cgcctgttgg cagtatcttc gacctgaagg    7200
```

```
ttggtaacac caagcacact ctccaagcca tcgagaccag ggtccttgct gggtccaaaa    7260
tgaccgtggc gcgcgtcgtc gatccgaccc ccacgccccc acccgcaccc gtgcccatcc    7320
ccctcccacc gaaggttttg gagaacggtc caaacgcttg gggggatgaa gaccgtttga    7380
ataaaaagag gaggcgcagg atggaagccc tcggcatcta tgttatgggc gggaaaaagt    7440
accagaaatt tgggacaag aattccggtg acgtgtttta tgaggaggtc cataacaaca     7500
cagatgagtg ggagtgcctc agagttggcg accctgccga ctttgaccct gagaagggaa    7560
ctttgtgtgg gcatgtcacc attgaagata gggcttacca tgtttacacc tccccatctg    7620
gtaagaaatt cctagtcccc gtcaacccag agaacggaag agttcaatgg gaggctgcaa    7680
agctttccgt tgagcaggcc cttggtatga tgaacgtcga cggcgagctg actgccaagg    7740
aactggagaa actgaaaaga ataattgaca aactccaggg cctgactaag gagcagtgtt    7800
taaactgcta gccgccagcg acttgacccg ctgtggtcgc ggcggcttgg ttgttactga    7860
aacagcggta aaaatagtca aatttcacaa ccggaccttc accctgggac ctgtgaattt    7920
aaaagtggcc agtgaggttg agctaaaaga cgcggttgag cacaaccaac acccggttgc    7980
gagaccgatc gatggtggag ttgtgctcct gcgttccgcg gttccttcgc ttatagacgt    8040
cttgatctcc ggtgctgatg catctcccaa gttacttgcc catcacgggc cgggaaacac    8100
tgggatcgat ggcacgctct gggattttga gtccgaagcc actaaagagg aagtcgcact    8160
cagtgcgcaa ataatacagg cttgtgacat taggcgcggc gacgctcctg aaattggtct    8220
cccttacaag ctgtaccctg ttaggggtaa ccctgagcgg gtgaaaggag ttctgcagaa    8280
tacaaggttt ggagacatac cttacaaaac ccccagtgac actggaagcc cagtgcacgc    8340
ggctgcctgc cttacgccca acgccactcc ggtgactgat gggcgctccg tcttggccac    8400
gaccatgccc cccgggtttg agttatatgt accgaccata ccagcgtctg tccttgatta    8460
ccttgactct aggcctgact gccctaaaca gctgacagag cacggctgcg aagatgccgc    8520
actgaaagac ctctctaaat atgacttgtc cacccaaggc tttgttttac ctggagttct    8580
tcgccttgtg cggaaatacc tgtttgccca tgtaggtaag tgcccacccg ttcatcggcc    8640
ttctacttac cctgctaaga attctatggc tggaataaat gggaacaggt tcccaaccaa    8700
ggacattcag agcgtccctg aaatcgacgt tctgtgcgca caggctgtgc gagaaaactg    8760
gcaaactgtc accccttgta ctcttaagaa acagtattgc gggaagaaga agactaggac    8820
catactcggc accaataact tcatcgcact agcccaccga gcagtgttga gtggtgttac    8880
ccagggcttc atgaaaaagg cgtttaactc gcccatcgcc ctcggaaaga acaagtttaa    8940
ggagctacag actccggtcc tgggcaggtg ccttgaagct gatctcgcat cctgcgatcg    9000
atccacgcct gcaattgtcc gctggtttgc cgccaacctt ctttatgaac ttgcctgtgc    9060
tgaagagcat ctaccgtcgt acgtgctgaa ctgctgccac gacttactgg tcacgcagtc    9120
cggcgcagtg actaagagag gtggcctgtc gtctggcgac ccgatcacct ctgtgtctaa    9180
caccatttat agtttggtga tctatgcaca gcatatggtg cttagttact tcaaaagtgg    9240
tcaccccat ggccttctgt tcttacaaga ccagctaaag tttgaggaca tgctcaaggt    9300
tcaaccctg atcgtctatt cggacgacct cgtgctgtat gccgagtctc ccaccatgcc    9360
aaactatcac tggtgggttg aacatctgaa tttgatgctg gggtttcaga cggacccaaa    9420
gaagacagca ttaacagact cgccatcatt tctaggctgt agaataataa atgggcgcca    9480
gctagtcccc aaccgtgaca ggatcctcgc ggccctcgcc tatcacatga aggcgagtaa    9540
```

```
tgtttctgaa tactatgcct cagcggctgc aatactcatg gacagctgtg cttgtttgga    9600
gtatgatact gaatggtttg aagaacttgt agttggaata gcgcagtgcg cccgcaagga    9660
cggctacagc tttcccggca cgccgttctt catgtccatg tgggaaaaac tcaggtccaa    9720
ttatgagggg aagaagtcga gagtgtgcgg gtactgcggg gccccggccc cgtacgctac    9780
tgcctgtggc ctcgacgtct gcatttacca cacccacttc caccagcatt gtccagtcac    9840
aatctggtgt ggccatccag cgggttctgg ttcttgtagt gagtgcaaat ccctgtagg     9900
gaaaggcaca agccctttag acggagtgtt ggaacaagtc ccgtataagc ccccacggac    9960
cgttatcatg catgtggagc agggtctcac ccccctttgat ccaggtagat accaaactcg  10020
ccgcggatta gtctctgtca ggcgtggaat taggggaaat gaagttgaac taccagacgg   10080
tgattatgct agcaccgcct tgctccctac ctgcaaagag atcaacatgg tcgctgtcgc   10140
ttccaacgta ttgcgcagca ggttcatcat cggcccaccc ggtgctggga aaacatactg   10200
gctccttcaa caggtccagg atggtgatgt tatttacaca ccaactcacc agaccatgct   10260
tgacatgatt agggctttgg ggacgtgccg gttcaacgtc ccggcaggca aacgctgca    10320
attccccgtc ccctcccgca ccggtccgtg ggttcgcatc ctagccggcg gttggtgtcc   10380
tggcaagaat tccttcctag atgaagcagc gtattgcaat caccttgatg ttttgaggct   10440
tcttagtaaa actaccctca cctgtctagg agacttcaag caactccacc cagtgggttt   10500
tgattctcat tgctatgttt ttgacatcat gcctcaaact caactgaaga ccatctggag   10560
gtttggacag aatatctgtg atgccattca gccagattac agggacaaac tcatgtccat   10620
ggtcaacaca acccgtgtga cctacgtgga aaaacctgtc aggtatgggc aggtcctcac   10680
cccctaccac agggaccgag aggacgacgc catcactatt gactccagtc aaggcgccac   10740
attcgatgtg gttacattgc atttgcccac taaagattca ctcaacaggc aaagagccct   10800
tgttgctatc accagggcaa gacacgctat ctttgtgtat gacccacaca ggcagctgca   10860
gggcttgttt gatcttcctg caaaaggcac acccgtcaac ctcgcagtgc accgcgacgg   10920
gcagctgatc gtgctggata gaaataacaa agaatgcacg gttgctcagg ctctaggcaa   10980
cggggataaa tttagggcca cagacaagcg tgttgtagat tctctccgcg ccatttgtgc   11040
tgatctagaa gggtcgagct ctccgctccc caaggtcgca cacaacttgg gattttattt   11100
ctcacctgat ttaacacagt tgctaaaact cccagtagaa cttgcacctc actggcccgt   11160
ggtgacaacc cagaacaatg aaaagtggcc agatcggctg gttgccagcc ttcgccctat   11220
ccataaatac agccgcgcgt gcatcggtgc cggctatatg gtgggcccctt cggtgttct   11280
aggcactcct gggtcgtgt catactatct cacaaaattt gttaagggcg aggctcaagt   11340
gcttccggag acggttttca gcaccggccg aattgaggta gactgccggg aatatcttga   11400
tgatcgggag cgagaagttg ctgcgtccct cccacacgct ttcattggcg acgtcaaagg   11460
cactaccgtt ggaggatgtc atcatgtcac ctccagatac ctcccgcgcg tccttcccaa   11520
ggaatcagtt gcggtagtcg gggtttcaag cccccggaaaa gccgcgaaag cattgtgcac   11580
actgacagat gtgtacctcc cagatcttga agcctatctc cacccggaga cccagtccaa   11640
gtgctggaaa atgatgttgg acttcaaaga agttcgacta atggtctgga agacaaaac    11700
agcctatttc caacttgaag gtcgctattt cacctggtat cagcttgcca gctatgcctc   11760
gtacatccgt gttcctgtca actctacggt gtacttggac cctgcatgg gccccgccct   11820
ttgcaacagg agagtcgtcg ggtccacccc ctggggggct gacctcgcgg tcacccctta   11880
tgattacggc gctaaaatta tcctgtctag cgcgtaccat ggtgaaatgc ccccggata   11940
```

```
caaaattctg gcgtgcgcgg agttctcgtt ggatgaccca gttaagtaca aacatacctg   12000 gggggtttgaa tcggatacag cgtatctgta tgagttcacc ggaaacggtg aggactggga   12060
ggattacaat gatgcgtttc gtgcgcgcca ggaagggaaa attttataagg ccactgccac   12120 cagcwtgaag ttttatttc ccccgggccc tgtcattgaa ccaactttag gcctgaattg   12180
aaatgaaatg gggtccatgc aaagcctttt tgacaaaatt ggtcaactt ttgtggatgc   12240 tttcacggaa ttcttggtgt ccattgttga tatcatcata ttttggcca ttttgtttgg   12300 cttcaccgtc gccggttggc tggtggtctt ttgcatcaga ttggtttgct ccgcgatact   12360
ccgtgcacgc cctgcctttc actctgagca gttacagaag atcctatgag gcctttcttt   12420
ccctgtgtca ggtggacatt cccacctggg gaatcaaaca tcctctgggg gtgctttggc   12480
accataaggt gtcaaccctg attgatgaaa tggtgtcgcg tcgaatgtac cgcatcatgg   12540
aaaaagcagg acaggctgcc tggaaacagg tggtgagcga ggccacgctg tctcgcatta   12600
gtagtttgga tgtggtggct cattttcaac atcttgccgc cgttgaagcc gagacctgta   12660
aatatttggc ctctcggcta cccatgctac acaacctgcg catgacgggg tcaaatgtaa   12720
ccatagtata taatggtact ttgaatcagg tgtttgccat tttcccgacc cctggttccc   12780
ggccaaagct tcatgatttt cagcaatggc tgatagctgt gcattcgtcc atattttcct   12840
ctgttgcagc ttcttgtact ctgtttgttg tactgtggtt gcgggtccca atgctacgta   12900 ctgttttgg tttccgctgg ttaggggcaa ttttccttc gagctcttgg tgaattacac   12960
ggtgtgccca ccttgcctca cccggcaagc agccgcacag cgctacgaac ctggcaaggc   13020
tctttggtgc agaattgggt acgatcgatg tgaggaggac gatcacgacg agctagggtt   13080
cgtgataccg tctggcctct ccagcgaagg ccacttgact agtgtttacg cctggttggc   13140 gttttttgtcc ttcagttaca cggcccagtt tcatcctgag atattcggga tagggaatgt   13200
gagcaaagtc tatgttgaca tcaaacacca attcatctgc gctgttcatg atgggcagaa   13260
caccaccttg ccccgccatg acaacttttc agccgtgttt cagacctatt accagcatca   13320
agtcgacggc ggcaattggt ttcacctaga atggctgcgt cccttctttt cctcttggtt   13380
ggttttaaat gtctcgtggt ttctcaggcg tttgcctgca agccatgttt cagttcgagt   13440 cttttcagaca ttaagaccaa caccaccgca gcagcgggct ttgctgtcct ccaggacatc   13500
agctgcctta ggcatggcga tccgtcctct gcggcgattc gcaaaagctc tcagtgccgc   13560
acggcgatag ggacacccgt gtatatcacc attacagcca atgtgacaga tgagaattat   13620
ttacactcct ctgatctcct catgctttct tcttgccttt tctatgcttc tgagatgagt   13680
gaaaagggat ttaaggtggt atttggcaat gtgtcaggca tcgtggctgt gtgtgttaat   13740
tttaccagct acgtccaaca tgtcagggac ttcacccaac gctccttggt ggtcgatcat   13800
gtgcggctgc tccatttcat gacacctgag gccatgaggt gggcaactgt tttagcctgt   13860 cttttttgcca ttctgttggc agtttgaatg tttaagtatg ttggggaaat gcttgaccgc   13920
gggttgctgc tcgcgattgc tttcttttg gtgtatcgtg ccgttctgtt ttgctgtgct   13980
cgtcaacgcc agctacagca gcagctctca tttacagttg atttataact tgacgctatg   14040
tgagctgaat ggtacagatt ggctggctaa taaatttgat tgggcagcgg agagtttgt   14100 catctttcct gtgttgaccc acatcgtttc ctatggtgca ctaaccacca gccacttcct   14160
tgacacagtt ggtctggtta ctgtgtctac cgccggggttt tatcatgggc ggtatgtcct   14220
gagtagcatc tacgcggtct gtgccctggg ctgcttaatt tgcttcgtca ttaggttggc   14280
```

-continued

| | |
|---|---|
| caataactgt atgtcctggc gctactcatg cacaagatac accaactttc ttctggacac | 14340 |
| taagggcaga ctctatcgtt ggcggtcgcc tgtcatcata gagaaagggg gtaaggtaga | 14400 |
| ggtcgaaggc catctgatcg acctcaaaag agttgtgctt gatggttccg cggcaacccc | 14460 |
| tttaaccaga gtttcagcgg aacaatgggg tcgtccctag acgactttg tcatgacagc | 14520 |
| acggctccac agaaggtgct cttggcgttt tctattactt acacgccagt gatgatatat | 14580 |
| gccctaaagg taagtcgcgg ccgattgctg gggcttctgc accttctgat cttcctgaat | 14640 |
| tgtgctttca ccttcgggta tatgacattc gcgcactttc agagtacaaa tagggtcgcg | 14700 |
| ctcactatgg gagcagtagt tgcactcctt tgggggtgt actcagccat agaaacttgg | 14760 |
| aggttcatca cctctagatg ccgtttgtgc ttgttaggcc gcaggtacat tctggcccct | 14820 |
| gcccaccacg ttgaaagtgc cgcaggcttt catccgatta cggcaaatga taaccacgca | 14880 |
| tttgtcgtcc ggcgtcccgg ctccactacg gttaacggca cattggtgcc cgggttgaag | 14940 |
| agcctcgtgt tgggtggcag aaaagctgta aacggggag tggttaacct tgttaaatat | 15000 |
| gccaaataac aacggcaaac agcagaagaa aagaagggg gatggccagc cagtcaatca | 15060 |
| gctgtgccag atgctgggta agatcatcgc ccagcaaaac cagtccagag gtaagggacc | 15120 |
| gggaaagaaa acaagaaga aaacccgga gaagccccat tttcctctgg cgactgaata | 15180 |
| tgacgtcaga caccacttta cccctagtga gcggcaattg tgcctgtcgt caatacagac | 15240 |
| tgcctttaat caaggcgctg gtacttgcac cctgtccgat tcagggagga taagttacac | 15300 |
| tgtggagttt agtttgccca cgcatcatac tgtgcgcctg attcgcgtca cagcatcacc | 15360 |
| ctcagcatga tgggctggca ttcttgaggc atctcagtgt ttgaattgga agaatgtgtg | 15420 |
| gtgaatggca ctgattgata ttgtgcctct aagtcaccta ttcaattagg gcgaccgtgt | 15480 |
| gggggtaaga tttaattggc gaaaaccatg cggccgaaat taaaaaaaaa aaaaaaaaaa | 15540 |
| aaa | 15543 |

<210> SEQ ID NO 2
<211> LENGTH: 49
<212> TYPE: DNA
<213> ORGANISM: Artificial Sequence
<220> FEATURE:
<223> OTHER INFORMATION: primer with T7

<400> SEQUENCE: 2
acatgcatgc taatacgact cactataggt atgacgtata ggtgttggc      49

<210> SEQ ID NO 3
<211> LENGTH: 37
<212> TYPE: DNA
<213> ORGANISM: Artificial Sequence
<220> FEATURE:
<223> OTHER INFORMATION: primer

<400> SEQUENCE: 3
acagcatgcg atgacgtata ggtgttggct ctatgcc      37

<210> SEQ ID NO 4
<211> LENGTH: 41
<212> TYPE: DNA
<213> ORGANISM: Artificial Sequence
<220> FEATURE:
<223> OTHER INFORMATION: anchor primer

<400> SEQUENCE: 4
gagtgacgag gactcgagcg cattaatttt tttttttttt t      41

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
cctcgtggcg gggatgaagt ga                                        22

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
ctgcccaggc catcatgtcc gaagtc                                    26

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
gccccgtcgg tctcagtctt gccattttt                                 29

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
accgaggctg taaaaggcaa gtgacc                                    26

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ctttccgttg agcaggccct tggtatga                                  28

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
gtacccgcac actctcgact tcttcccctc at                             32

<210> SEQ ID NO 11
<211> LENGTH: 27
<212> TYPE: DNA
<213> ORGANISM: Artificial Sequence
<220> FEATURE:

-continued

<223> OTHER INFORMATION: primer

<400> SEQUENCE: 11
tcgtcctatc catgagtata gccgcgc　　　　　　　　　　　　　　　　27

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
cagcgctacg aacctggcaa ggt　　　　　　　　　　　　　　　　23

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
ttgccgccgt cgacttgatg ctggtaat　　　　　　　　　　　　　　28

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
caattaaatc ttaccccccac acggtcg　　　　　　　　　　　　　　27

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
ttaattaatt taaatggcgc gccaatgaaa tggggtccat gc　　　　　　　42

<210> SEQ ID NO 16
<211> LENGTH: 44
<212> TYPE: DNA
<213> ORGANISM: Artificial Sequence
<220> FEATURE:
<223> OTHER INFORMATION: primer

<400> SEQUENCE: 16
ggcgcgccat ttaaattaat taatcaattc aggcctaaag ttgg　　　　　　44

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
atttaaatta attaaggcgc gcccacgctg tctcgcatta gt　　　　　　　42

<210> SEQ ID NO 18
<211> LENGTH: 41
<212> TYPE: DNA
<213> ORGANISM: Artificial Sequence
<220> FEATURE:
<223> OTHER INFORMATION: primer

<400> SEQUENCE: 18
ggcgcgcctt aattaattta aatgtatcgc ggtgcaaacc g                41

<210> SEQ ID NO 19
<211> LENGTH: 41
<212> TYPE: DNA
<213> ORGANISM: Artificial Sequence
<220> FEATURE:
<223> OTHER INFORMATION: primer

<400> SEQUENCE: 19
ggcgcgcctt aattaattta aatataattc tcatctgtca c                41

<210> SEQ ID NO 20
<211> LENGTH: 41
<212> TYPE: DNA
<213> ORGANISM: Artificial Sequence
<220> FEATURE:
<223> OTHER INFORMATION: primer

<400> SEQUENCE: 20
atttaaatta attaaggcgc gcccgatcag tgcggctgct c                41

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
agcatgatgg gctggcatat gtcttgaggc                             30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
gcctcaagat agatgccagc ccatcatgct                             30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
tgtcctggcg ctacgcgtgc accagataca                             30

<210> SEQ ID NO 24
<211> LENGTH: 28
<212> TYPE: DNA
<213> ORGANISM: Artificial Sequence
<220> FEATURE:
<223> OTHER INFORMATION: primer -continued

```
<400> SEQUENCE: 24
tgtatctggt gcacgtagcg ccaggaca                                          28

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
gggcgcgcca ttcttgaggc atctcagtgt tttg                                   34

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
cttaattaaa tcatgctgtg gtgatgctg                                         29

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
ccttaattaa tgacgtatcc agggaggcg                                         29

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
aggcgcgcct tagggtttaa gtgggggtc tttaag                                  36
```